(12) United States Patent
Wang et al.

(10) Patent No.: US 11,492,413 B2
(45) Date of Patent: Nov. 8, 2022

(54) SWITCHABLE ANTIBODY CONJUGATE

(71) Applicant: Temple University—Of The Commonwealth System of Higher Education, Philadelphia, PA (US)

(72) Inventors: Rongsheng E. Wang, Philadelphia, PA (US); Zhigang Lyu, Philadelphia, PA (US); Haley L. Wissler, North Attleboro, MA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 914 days.

(21) Appl. No.: 16/208,768

(22) Filed: Dec. 4, 2018

(65) Prior Publication Data

US 2019/0211111 A1   Jul. 11, 2019

Related U.S. Application Data

(60) Provisional application No. 62/594,069, filed on Dec. 4, 2017.

(51) Int. Cl.
*C07K 16/32* (2006.01)
*C07K 16/14* (2006.01)
*C07K 16/28* (2006.01)
*A61P 35/00* (2006.01)
*A61K 47/68* (2017.01)

(52) U.S. Cl.
CPC .............. *C07K 16/32* (2013.01); *A61K 47/68* (2017.08); *A61P 35/00* (2018.01); *C07K 16/14* (2013.01); *C07K 16/2803* (2013.01); *C07K 2317/51* (2013.01); *C07K 2317/515* (2013.01); *C07K 2317/55* (2013.01)

(58) Field of Classification Search
None
See application file for complete search history.

(56) References Cited

PUBLICATIONS

Rodgers et al., Proc. Natl. Acad. Sci. U.S.A. 113, 2016, E459-468 (Year: 2016).*
Adumeau et al., "Site-Specifically Labeled Immunoconjugates for Molecular Imaging—Part 1: Cysteine Residues and Glycans," Mol. Imaging Biol. 2016, 18 (1), 1-17.
Adumeau et al., "Site-Specifically Labeled Immunoconjugates for Molecular Imaging—Part 2: Peptide Tags and Unnatural Amino Acids," Mol. Imaging Biol. 2016, 18 (2), 153-165.
Axup et al., "Synthesis of site-specific antibody-drug conjugates using unnatural amino adds," Proc. Natl. Acad. Sci. U. S. A. 2012, 109 (40), 16101-16106.
Cook et al., "Pretargeted PET Imaging Using a Site-Specifically Labeled Immunoconjugate," Bioconjug. Chem. 2016, 27 (8), 1789-1795.

(Continued)

*Primary Examiner* — Karl J Puttlitz
(74) *Attorney, Agent, or Firm* — Riverside Law LLP

(57) ABSTRACT

The present invention relates to a Fab fragment based switchable antibody system for generating site-specific antibody conjugates. Methods are described for the attachment of molecules to specific sites the Fab fragment and for the attachment of the Fab fragment to a target molecule (e.g., an antibody) directed against any desired target antigen (tumor, bacterial, fungal, viral, parasitic etc.) The attachment is via binding of the Fab fragment to an epitope linked to the target molecule.

6 Claims, 19 Drawing Sheets

Specification includes a Sequence Listing.

(56) References Cited

PUBLICATIONS

Du et al., "Differential cellular internalization of anti-CD19 and -CD22 immunotoxins results in different cytotoxic activity," Cancer Res. 2008, 68 (15), 6300-6305.
Ehlerding et al., "Molecular Imaging of Immunotherapy Targets in Cancer," J. Nucl. Med. 2016, 57 (10), 1487-1492.
Gill et al., "Production of anti-digoxigenin antibody HRP conjugate for PCE-ELISA DIG detection system," J. Immunoassay Immunochem. 2006, 27 (4), 303-3¬18.
Guldbrandsen et al., "Nuclear Molecular Imaging Strategies in Immune Checkpoint Inhibitor Therapy," Diagnostics (Basel) 2017, 7(2), 23.
Hernandez et al., "CD146-targeted immunoPET and NIRF Imaging of Hepatocellular Carcinoma with a Dual-Labeled Monoclonal Antibody," Theranostics 2016, 6 (11), 1918-1933.
Hutchins et al., "Selective formation of covalent protein heterodimers with an unnatural amino add," Chem. Biol. 2011, 18 (3), 299-303.
Junutula et al., "Site-specific conjugation of a cytotoxic drug to an antibody improves the therapeutic index," Nat. Biotechnol. 2008, 26 (8), 925-932.
Kazane et al., "Site-specific DNA-antibody conjugates for specific and sensitive immuno-PCR," Proc. Natl. Acad. Sci. U. S. A. 2012, 109 (10), 3731-3736.
Kim et al., "Synthesis of bispecific antibodies using genetically encoded unnatural amino acids," J Am Chem Soc 2012, 134 (24), 9918-9921.
Kularatne et al., "A CXCR4-targeted site-specific antibody-drug conjugate," Angew. Chem. Int. Ed. Engl. 2014, 53 (44), 11863-11867.
Lewis Phillips et al., "Targeting HER2-positive breast cancer with trastuzumab-DM1, an antibody-cytotoxic drug conjugate," Cancer Res. 2008, 68 (22), 9280-9290.
Lu et al., "Site-specific antibody-polymer conjugates for siRNA delivery," J. Am. Chem. Soc. 2013, 135 (37), 13885-13891.
Sano et al., "Immuno-PCR: very sensitive antigen detection by means of specific antibody-DNA conjugates," Science 1992, 258 (5079), 120-122.
Schumacher et al., "Current Status: Site-Specific Antibody Drug Conjugates," J. Clin. Immunol. 2016, 36 Suppl 1, 100-107.
Shen et al., "Conjugation site modulates the in vivo stability and therapeutic activity of antibody-drug conjugates," Nat. Biotechnol. 2012, 30 (2), 184-189.
Wang et al., "An immunosuppressive antibody-drug conjugate," J. Am. Chem. Soc. 2015, 137 (9), 3229-3232.
Wang et al., "Antibody-based imaging of HER-2: moving into the clinic," Curr. Mol. Med. 2013, 13 (10), 1523-1537.
Wang et al., "Rational design of a Kv1.3 channel-blocking antibody as a selective immunosuppressant," Proc Natl Acad Sci U S A 2016, 113 (41), 11501-11506.
Wu and Schultz, "Synthesis at the interface of chemistry and biology," J. Am. Chem. Soc. 2009, 131 (35), 12497-12515.
Xiao et al., "At the Interface of Chemical and Biological Synthesis: An Expanded Genetic Code," Cold Spring Harb. Perspect. Biol. 2016, 8 (9).
Yi et al., "Near-infrared fluorescent probes in cancer imaging and therapy: an emerging field," Int. J. Nanomedicine 2014, 9, 1347-1365.
Zahnd et al., "Directed in vitro evolution and crystallographic analysis of a peptide-binding single chain antibody fragment (ScFv) with low picomolar affinity," J. Biol. Chem. 2004, 279 (18), 18870-18877.
Zhang et al., "Near-infrared Molecular Probes for In Vivo Imaging," Curr. Protoc. Cytom. 2012, Chapter 12, Unit12 27.
Zola et al., "Preparation and characterization of a chimeric CD19 monoclonal antibody," Immunol Cell Biol 1991, 69 ( Pt 6), 411-422.

* cited by examiner

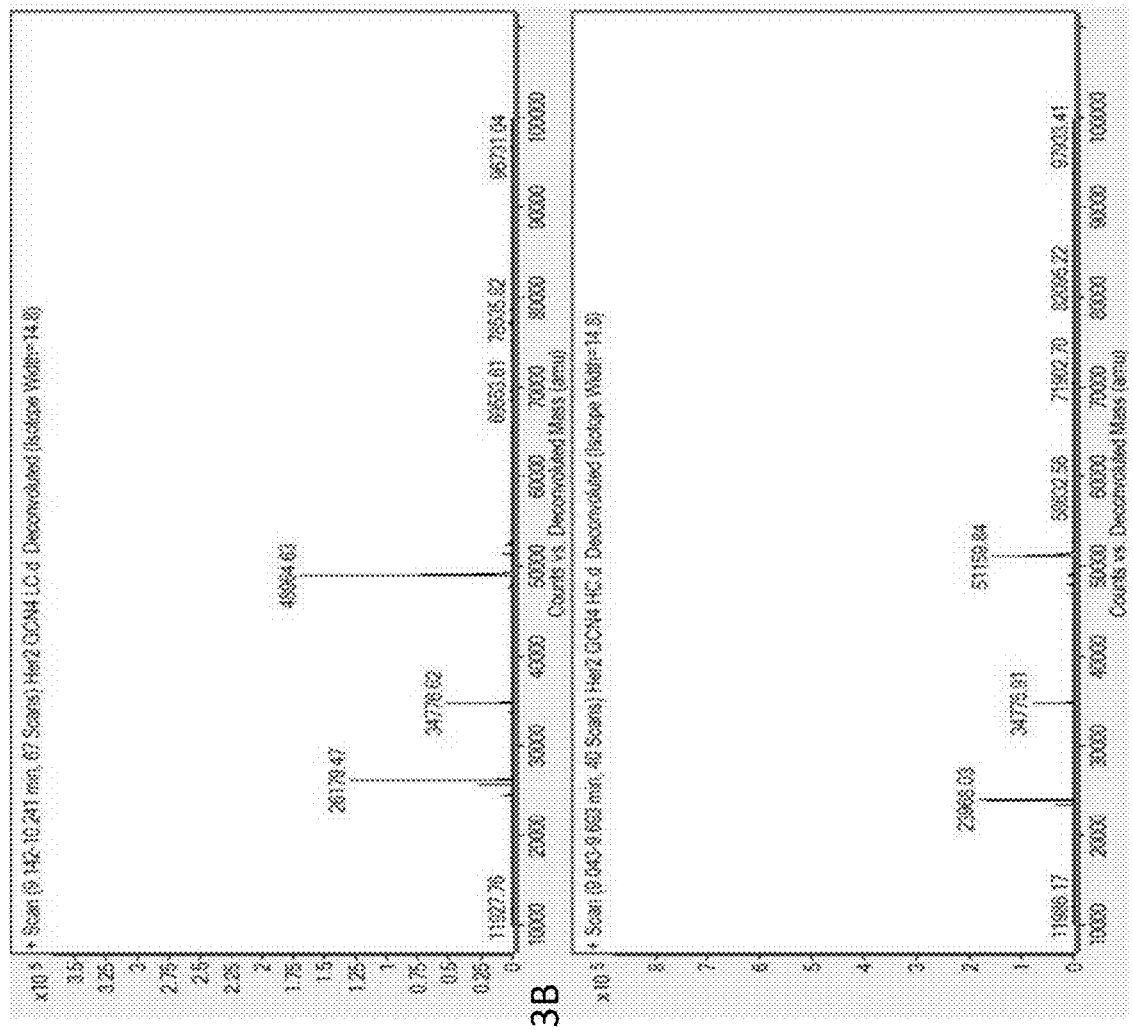

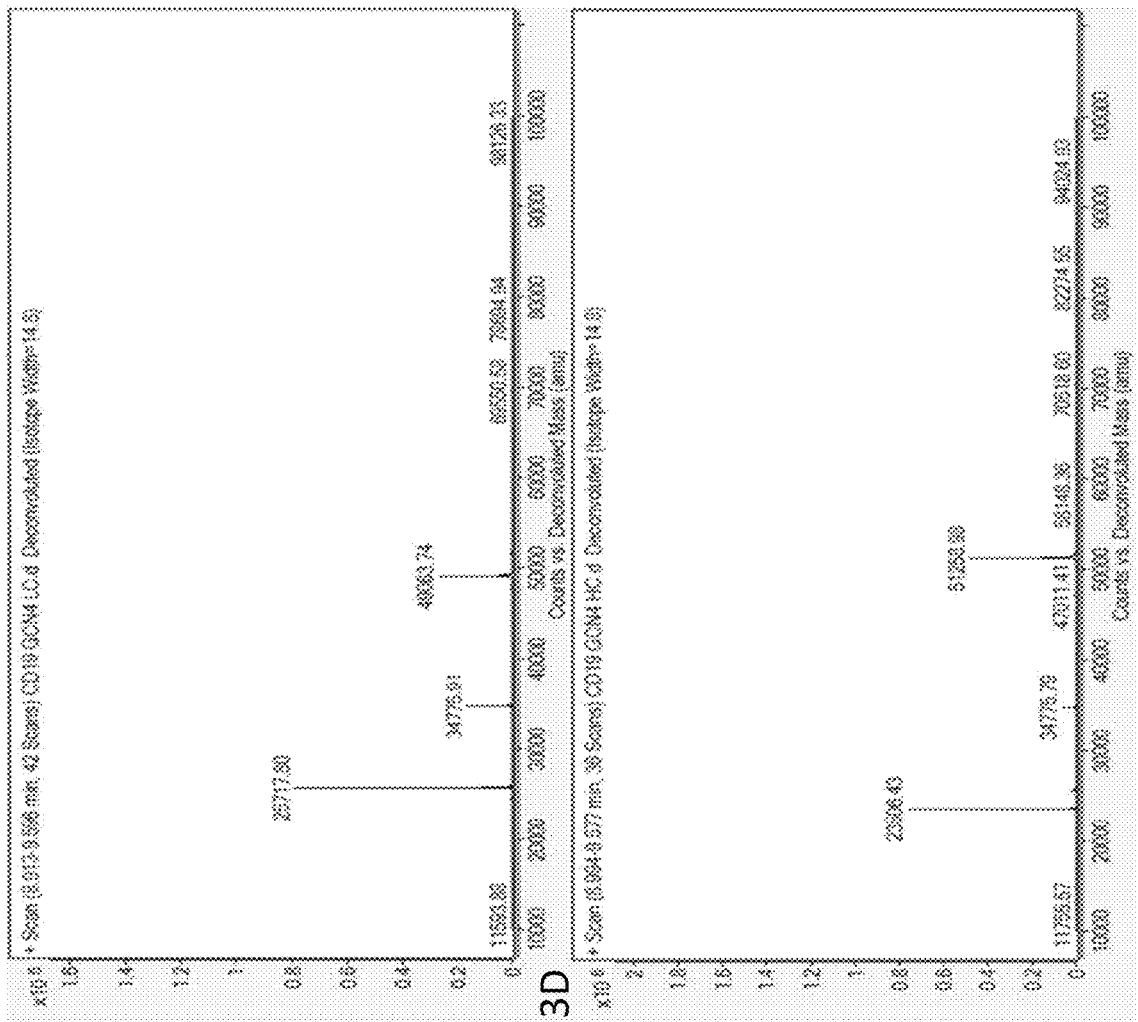

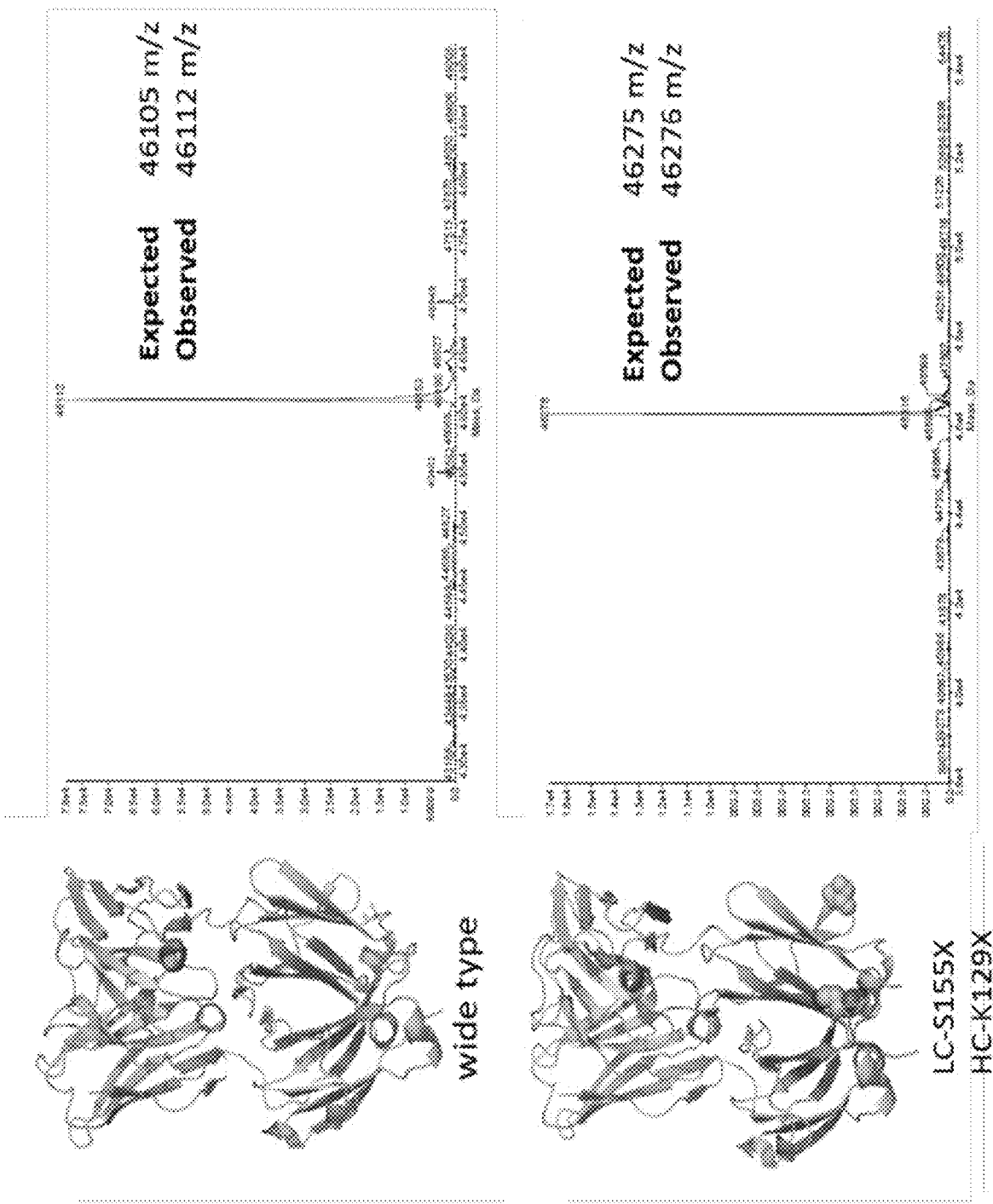

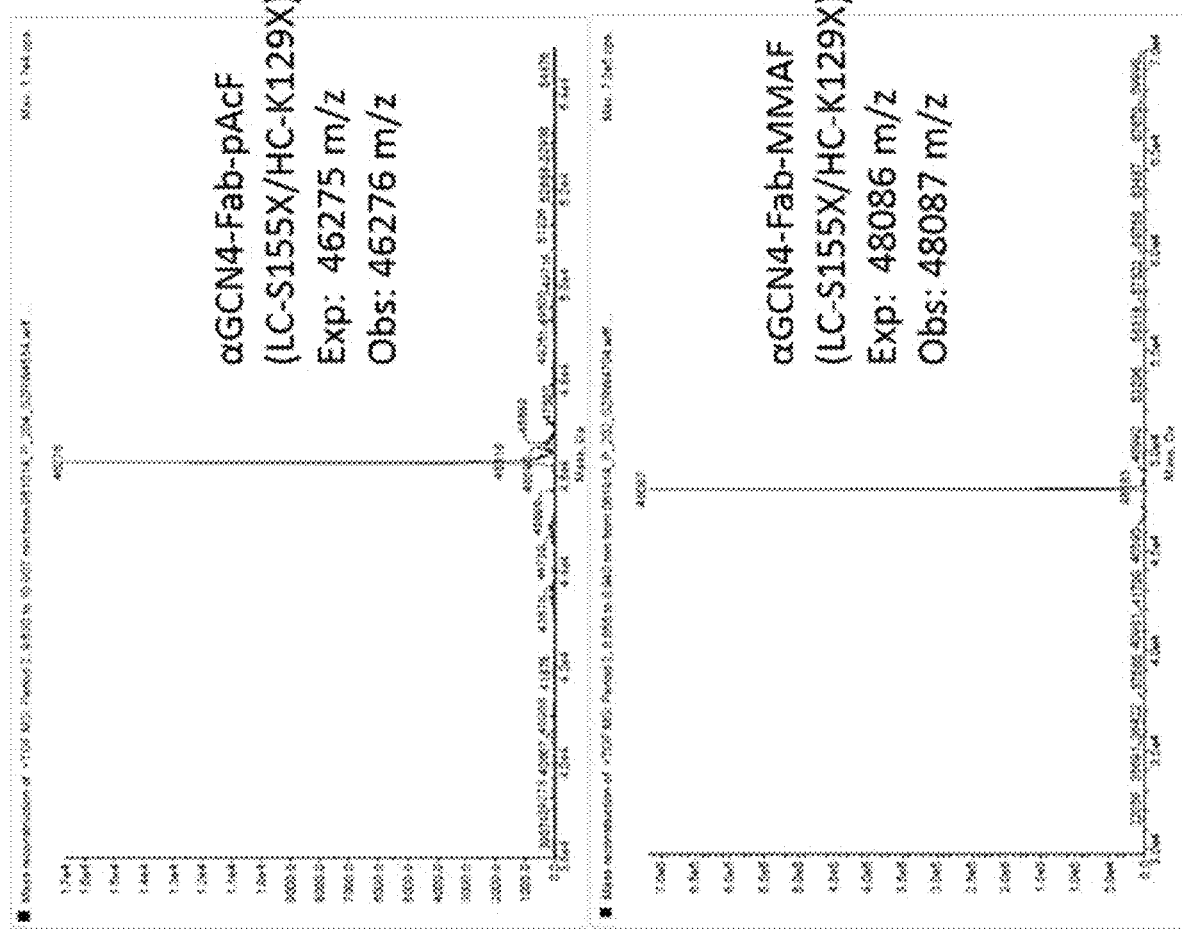
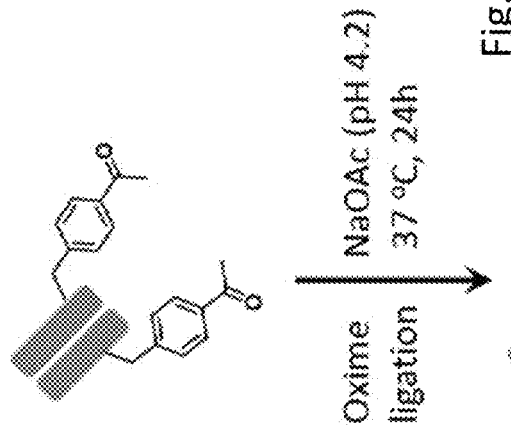
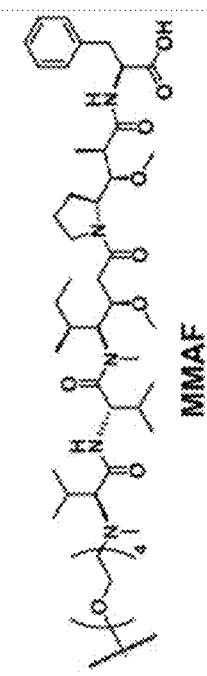
Fig. 9A
Fig. 9B
Fig. 9C

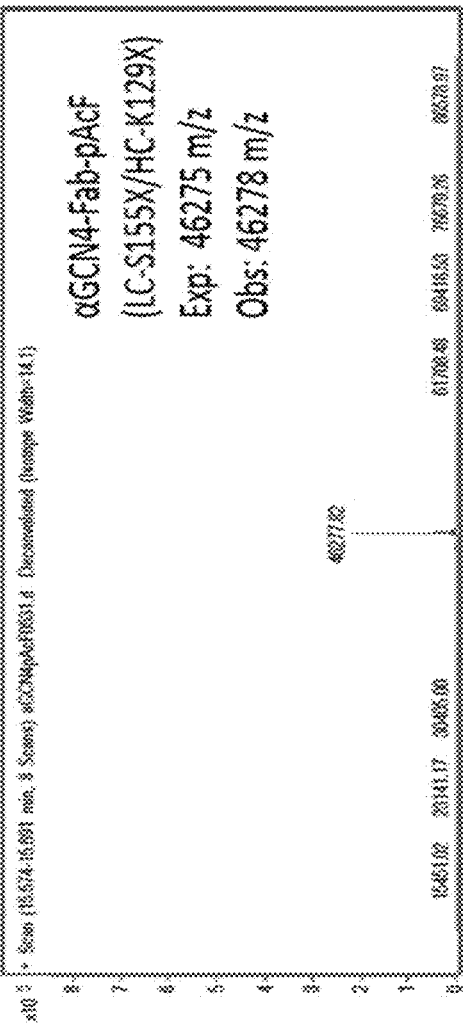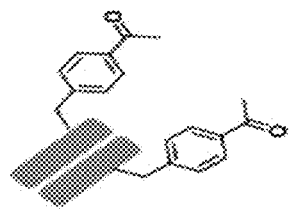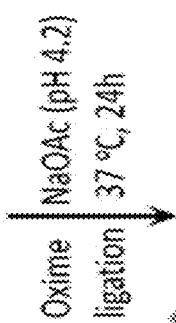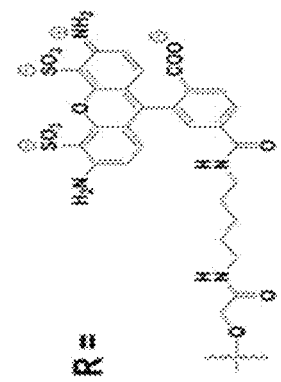
Fig. 12A, Fig. 12B, Fig. 12C

αGCN4-Fab-BCN
(LC-S155X/HC-K129X)
Exp: 47040 m/z
Obs: 47041 m/z

αGCN4-Fab-Cy7
(LC-S155X/HC-K129X)
Exp: 48620 m/z
Obs: 48623 m/z

SEQUENCE LISTING

```
<160> NUMBER OF SEQ ID NOS: 13

<210> SEQ ID NO 1
<211> LENGTH: 42
<212> TYPE: DNA
<213> ORGANISM: Artificial Sequence
<220> FEATURE:
<223> OTHER INFORMATION: Chemically Synthesized, nucleotide sequence of
      the GCN4 peptide

<400> SEQUENCE: 1
aattatcatc ttgaaaatga ggtcgctcgt ctcaagaaac tc                     42
```

```
<210> SEQ ID NO 2
<211> LENGTH: 14
<212> TYPE: PRT
<213> ORGANISM: Artificial Sequence
<220> FEATURE:
<223> OTHER INFORMATION: Chemically Synthesized, GCN4 peptide

<400> SEQUENCE: 2

Asn Tyr His Leu Glu Asn Glu Val Ala Arg Leu Lys Lys Leu
1               5                   10

<210> SEQ ID NO 3
<211> LENGTH: 214
<212> TYPE: PRT
<213> ORGANISM: Artificial Sequence
<220> FEATURE:
<223> OTHER INFORMATION: Chemically Synthesized, Anti-Her2 trastuzumab
      light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 237
<212> TYPE: PRT
<213> ORGANISM: Artificial Sequence
<220> FEATURE:
<223> OTHER INFORMATION: Chemically Synthesized, Anti-Her2 trastuzumab
      light chain GCN4

<400> SEQUENCE: 4

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Ser Asn Tyr His
                165                 170                 175

Leu Glu Asn Glu Val Ala Arg Leu Lys Lys Leu Gly Gly Gly Ser
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys
225                 230                 235

<210> SEQ ID NO 5
<211> LENGTH: 223
<212> TYPE: PRT
<213> ORGANISM: Artificial Sequence
<220> FEATURE:
<223> OTHER INFORMATION: Chemically Synthesized, Anti-Her2 trastuzumab
      heavy chain (up to CH1)

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala

```
                    130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
210                 215                 220

<210> SEQ ID NO 6
<211> LENGTH: 245
<212> TYPE: PRT
<213> ORGANISM: Artificial Sequence
<220> FEATURE:
<223> OTHER INFORMATION: Chemically Synthesized, Anti-Her2 trastuzumab
      heavy chain GCN4 (up to CH1)

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Gly Gly Gly Gly Ser Asn Tyr His Leu Glu Asn Glu Val
                180                 185                 190

Ala Arg Leu Lys Lys Leu Gly Gly Gly Ser Leu Tyr Ser Leu Ser
            195                 200                 205

Ser Val Val Thr Val Pro Ser Ser Leu Gly Thr Gln Thr Tyr Ile
        210                 215                 220

Cys Asn Val Asn His Lys Pro Ser Asn Thr Lys Val Asp Lys Lys Val
225                 230                 235                 240

Glu Pro Lys Ser Cys
                245

<210> SEQ ID NO 7
<211> LENGTH: 214
```

```
<212> TYPE: PRT
<213> ORGANISM: Artificial Sequence
<220> FEATURE:
<223> OTHER INFORMATION: Chemically Synthesized, Anti-CD19 FMC63 light
      chain

<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 237
<212> TYPE: PRT
<213> ORGANISM: Artificial Sequence
<220> FEATURE:
<223> OTHER INFORMATION: Chemically Synthesized, Anti-CD19 FMC63 light
      chain GCN4

<400> SEQUENCE: 8

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95
```

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Ser Asn Tyr His
                165                 170                 175

Leu Glu Asn Glu Val Ala Arg Leu Lys Lys Leu Gly Gly Gly Ser
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 9
<211> LENGTH: 223
<212> TYPE: PRT
<213> ORGANISM: Artificial Sequence
<220> FEATURE:
<223> OTHER INFORMATION: Chemically Synthesized, Anti-CD19 FMC63 heavy
      chain (up to CH1)

<400> SEQUENCE: 9

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 10
<211> LENGTH: 245
<212> TYPE: PRT
<213> ORGANISM: Artificial Sequence
<220> FEATURE:
<223> OTHER INFORMATION: Chemically Synthesized, Anti-CD19 FMC63 heavy
      chain GCN4

<400> SEQUENCE: 10

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Gly Gly Gly Gly Ser Asn Tyr His Leu Glu Asn Glu Val
            180                 185                 190

Ala Arg Leu Lys Lys Leu Gly Gly Gly Ser Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys
                245

<210> SEQ ID NO 11
<211> LENGTH: 215
<212> TYPE: PRT
<213> ORGANISM: Artificial Sequence
<220> FEATURE:
<223> OTHER INFORMATION: Chemically Synthesized, Anti-GCN4 Fab light
      chain

<400> SEQUENCE: 11

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

```
Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Val Leu Trp Tyr Ser Asp
                 85                  90                  95

His Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 12
<211> LENGTH: 221
<212> TYPE: PRT
<213> ORGANISM: Artificial Sequence
<220> FEATURE:
<223> OTHER INFORMATION: Chemically Synthesized, Anti-GCN4 Fab heavy chain

<400> SEQUENCE: 12

```
Asp Val Gln Leu Gln Glu Ser Gly Pro Gly Leu Val Ala Pro Ser Gln
 1               5                  10                  15

Ser Leu Ser Ile Thr Cys Thr Val Ser Gly Phe Leu Leu Thr Asp Tyr
                20                  25                  30

Gly Val Asn Trp Val Arg Gln Ser Pro Gly Lys Gly Leu Glu Trp Leu
            35                  40                  45

Gly Val Ile Trp Gly Asp Gly Ile Thr Asp Tyr Asn Ser Ala Leu Lys
        50                  55                  60

Ser Arg Leu Ser Val Thr Lys Asp Asn Ser Lys Ser Gln Val Phe Leu
 65                  70                  75                  80

Lys Met Asn Ser Leu Gln Ser Gly Asp Ser Ala Arg Tyr Tyr Cys Val
                 85                  90                  95

Thr Gly Leu Phe Asp Tyr Trp Gly Gln Gly Thr Thr Leu Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
```

-continued

```
                180                 185                 190
Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr
    210                 215                 220

<210> SEQ ID NO 13
<211> LENGTH: 5
<212> TYPE: PRT
<213> ORGANISM: Artificial Sequence
<220> FEATURE:
<223> OTHER INFORMATION: Chemically Synthesized, G4S linker

<400> SEQUENCE: 13

Gly Gly Gly Gly Ser
1               5
```

SWITCHABLE ANTIBODY CONJUGATE

CROSS REFERENCE TO RELATED APPLICATIONS

This application claims priority to U.S. Provisional Application No. 62/594,069, filed Dec. 4, 2017 which is hereby incorporated by reference herein in its entirety.

BACKGROUND OF THE INVENTION

Over the past decades, antibody conjugates with small molecules (Hernandez et al., Theranostics 2016, 6 (11), 1918-1933; Lewis Phillips et al., Cancer Res. 2008, 68 (22), 9280-9290; Wang et al., J. Am. Chem. Soc. 2015, 137 (9), 3229-3232), oligomers (Sano et al., Science 1992, 258 (5079), 120-122), and proteins (Gill et al., J. Immunoassay Immunochem. 2006, 27 (4), 303-318) have been extensively pursued for immuno-assay, imaging-based detection and diagnosis, as well as therapeutic development. In particular, antibody-drug conjugates (ADCs) emerge as a promising class of immunotherapeutic, with trastuzumab-DM1, brentuximab vedotin, and inotuzumab-ozogamicin being recently FDA-approved for treatment of breast cancer, Hodgkin's lymphoma, and acute lymphoblastic leukemia, respectively (Lewis Phillips et al., Cancer Res. 2008, 68 (22), 9280-9290; Wang et al., J. Am. Chem. Soc. 2015, 137 (9), 3229-3232). The most common antibody conjugation method relies on a random reaction with surface-exposed cysteines or lysines which results in a heterogeneous mixture of conjugates with distinct stabilities, efficacies, and pharmacokinetics/pharmacodynamics (Adumeau et al., Mol. Imaging Biol. 2016, 18 (1), 1-17; Schumacher et al., J. Clin. Immunol. 2016, 36 Suppl 1, 100-107). With the use of site-specific conjugation, a precise control of sites and stoichiometry, homogeneous antibody conjugates can be generated to possess improved signal-to-noise ratios, efficacy, pharmacokinetics, and therapeutic indexes relative to conventionally-made random conjugates (Adumeau et al., Mol. Imaging Biol. 2016, 18 (1), 1-17; Junutula et al., Nat. Biotechnol. 2008, 26 (8), 925-932; Shen et al., Nat. Biotechnol. 2012, 30 (2), 184-189). One method for synthesizing site-specific antibody conjugates involves the amber-suppression mediated genetic incorporation of unnatural amino acids (UAAs) (Wu and Schultz, J. Am. Chem. Soc. 2009, 131 (35), 12497-12515), in which a pair of orthogonal tRNA/aminoacyltRNA synthetase specific for the UAA were evolved in order to incorporate the UAA based on the amber codon TAG to the selected sites of a protein (Wu and Schultz, J. Am. Chem. Soc. 2009, 131 (35), 12497-12515; Adumeau et al., Mol. Imaging Biol. 2016, 18 (2), 153-165; Lu et al., J. Am. Chem. Soc. 2013, 135 (37), 13885-13891). To date, approximately 200 structurally distinct UAAs have been systematically added to proteins (Xiao et al., Cold Spring Harb. Perspect. Biol. 2016, 8 (9)).

A typical UAA with the desired chemical reactivity is p-acetylphenylalanine (pAcF), which has been successfully coupled to small molecules, oligonucleotides, polymers, or proteins of interest via a stable oxime linkage (Lu et al., J. Am. Chem. Soc. 2013, 135 (37), 13885-13891; Axup et al., Proc. Natl. Acad. Sci. U.S.A. 2012, 109 (40), 16101-16106; Hutchins et al., Chem. Biol. 2011, 18 (3), 299-303; Kazane et al., Proc. Natl. Acad. Sci. U.S.A 2012, 109 (10), 3731-3736; Kularatne et al., Angew. Chem. Int. Ed. Engl. 2014, 53 (44), 11863-11867). Yet the strategy based on UAA is deemed intrinsically complicated, costly and consuming in terms of time and labor (Schumacher et al., J. Clin. Immunol. 2016, 36 Suppl 1, 100-107; Adumeau et al., Mol. Imaging Biol. 2016, 18 (2), 153-165). More importantly, the yields of UAA mutants, conjugation efficiency, and conjugate stability vary and largely depend on each individual antibody (Adumeau et al., Mol. Imaging Biol. 2016, 18 (1), 1-17; Schumacher et al., J. Clin. Immunol. 2016, 36 Suppl 1, 100-107; Adumeau et al., Mol. Imaging Biol. 2016, 18 (2), 153-165; Axup et al., Proc. Natl. Acad. Sci. U.S.A 2012, 109 (40), 16101-16106; Kularatne et al., Angew. Chem. Int. Ed. Engl. 2014, 53 (44), 11863-11867).

Thus, there is a need in the art for an orthogonal switch as a general and effective strategy to endow versatility to a single antibody conjugate, which facilitates the application of UAA-based site-specific antibody conjugates for a host of therapeutic uses. The present invention satisfies this unmet need.

SUMMARY OF THE INVENTION

In one embodiment, the invention relates to a composition comprising an immunoconjugate molecule, wherein the immunoconjugate molecule comprises a polypeptide component, wherein the polypeptide component comprises an antigen-binding domain, and at least one conjugated molecule.

In one embodiment, the polypeptide component is an anti-GCN4 Fab fragment. In one embodiment, the anti-GCN4 Fab fragment comprises a light chain amino acid sequence as set forth in SEQ ID NO:11. In one embodiment, the anti-GCN4 Fab fragment comprises a heavy chain amino acid sequence as set forth in SEQ ID NO:12. In one embodiment, the anti-GCN4 Fab fragment comprises at least one non-naturally encoded amino acid, wherein the non-naturally encoded amino acid is not within the antigen-binding domain.

In one embodiment, the polypeptide component comprises at least one non-naturally encoded amino acid. In one embodiment, the at least one non-naturally encoded amino acid is p-azido-L-phenylalanine (pAzF), p-iodo-phenylalanine, p-bromophenylalanine, p-amino-L-phenylalanine, or p-acetylphenylalanine (pAcF). In one embodiment, the polypeptide component comprises a light chain amino acid sequence as set forth in SEQ ID NO:11 further comprising at least one non-naturally encoded amino acid selected from the group consisting of S193pAcF, S155pAcF, and G202pAcF. In one embodiment, the polypeptide component comprises a heavy chain amino acid sequence as set forth in SEQ ID NO:12 further comprising at least one non-naturally encoded amino acid selected from the group consisting of K129pAcF and K132pAcF.

In one embodiment, at least one conjugated molecule is a protein, a polypeptide, a detectable molecule, a cytotoxin, a radioactive agent, an anti-tumor agent or a therapeutic agent.

In one embodiment, at least one conjugated molecule is non-cleavable auristatin F (MMAF), alkoxy-amine-derivatized Alexa Fluor 488 (AF488), or cyanine 7 (Cy7) dye.

In one embodiment, the invention relates to a composition comprising a targeting molecule, wherein the targeting molecule comprises a targeting domain for binding to a target of interest and a immunoconjugate-antigen domain for recognition by an antigen binding domain of an immunoconjugate molecule.

In one embodiment, the targeting domain is an antibody, a protein, an aptamer, a peptide ligand, or a non-peptidyl ligand.

In one embodiment, the targeting molecule is an antibody linked to an immunoconjugate-antigen domain.

In one embodiment, the antibody is specific for a tumor antigen.

In one embodiment, the immunoconjugate-antigen domain comprises a GCN4 peptide.

In one embodiment, the targeting molecule is selected from the group consisting of an anti-Her2 antibody having a light chain as set forth in SEQ ID NO:4 and an anti-Her2 antibody having a heavy chain variable region as set forth in SEQ ID NO:6, an anti-CD19 antibody having a light chain as set forth in SEQ ID NO:8, and an anti-CD19 antibody having a heavy chain variable region as set forth in SEQ ID NO:10.

In one embodiment, the invention relates to a composition comprising a site-specific conjugate molecule, wherein the site-specific conjugate molecule comprises an immunoconjugate molecule fused to a targeting molecule through the interaction of an antigen binding domain of a polypeptide component of the immunoconjugate molecule with an immunoconjugate-antigen domain of the targeting molecule.

In one embodiment, the polypeptide component of the immunoconjugate molecule is an anti-GCN4 Fab fragment and the immunoconjugate-antigen domain is a GCN4 peptide.

In one embodiment, the invention relates to a method of detecting a target molecule in a sample from a subject comprising the steps of a) contacting the sample with at least one composition comprising a targeting molecule, wherein the targeting molecule comprises a targeting domain for binding to a target of interest and an immunoconjugate-antigen domain for recognition by an antigen binding domain of an immunoconjugate molecule, b) contacting the sample with at least one composition comprising an immunoconjugate molecule, wherein the immunoconjugate molecule comprises an antigen-binding domain comprising at least one non-naturally encoded amino acid and at least one conjugated molecule and c) analyzing the sample.

In one embodiment, at least one conjugated molecule is a detectable molecule.

In one embodiment, the invention relates to a method of treating a disease or disorder in a subject in need thereof, the method comprising the steps of: a) administering to the subject at least one composition comprising a targeting molecule, wherein the targeting molecule comprises a targeting domain for binding to a target of interest and an immunoconjugate-antigen domain for recognition by an antigen binding domain of an immunoconjugate molecule, wherein the targeting molecule specifically binds to an antigen associated with the disease or disorder; and b) administering to the subject at least one composition comprising an immunoconjugate molecule, wherein the immunoconjugate molecule comprises a polypeptide component comprising an antigen-binding domain and at least one conjugated molecule, wherein at least one conjugated molecule is a therapeutic agent for the treatment of the disease or disorder.

In one embodiment, the targeting molecule is fused to the immunoconjugate molecule prior to administration.

In one embodiment, the disease or disorder is cancer.

In one embodiment, the disease or disorder is a breast cancer, and wherein the therapeutic agent comprises a therapeutic agent for treatment of breast cancer.

In one embodiment, the disease or disorder is a Ramos cancer, and wherein the therapeutic agent comprises a therapeutic agent for treatment of Ramos cancer.

BRIEF DESCRIPTION OF THE DRAWINGS

The following detailed description of exemplary embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 3A through FIG. 3D, depicts the results of exemplary experiments demonstrating ESI-MS spectra of the GCN4 fusion antibodies treated with PNGase F (New England Biolab, MS peak at 34776 m/z) to remove N-glycans and 10 mM DTT to afford light chains (LC) and heavy chains (HC). FIG. 3A depicts an ESI-MS spectra of αHer2-LC-GCN4. FIG. 3B depicts an ESI-MS spectra of αHer2-HC-GCN4. FIG. 3C depicts an ESI-MS spectra of αCD19-LC-GCN4. FIG. 3D depicts an ESI-MS spectra of αCD19-HC-GCN4.

FIG. 4A depicts the results of exemplary experiments demonstrating sites of mutation in αGCN4 Fab based on the crystal structure of a Fab with a lambda light chain (PDB: 4FQH) FIG. 4B depicts the results of an exemplary ELISA analysis of αGCN4-Fab mutants captured by GCN4 antigen and detected with anti-human λ-HRP. Error bar represents the standard deviation of three replicates.

FIG. 6A through FIG. 6D, depicts the results of exemplary experiments demonstrating ESI-MS spectra of wide type and double-mutated αGCN4 Fab's. FIG. 6A depicts an ESI-MS spectra of wild type αGCN4. FIG. 6B depicts an ESI-MS spectra of αGCN4 comprising a HC K129X and LC S155X mutation. FIG. 6C depicts an ESI-MS spectra of αGCN4 comprising a HC K129X and LC S193X mutation. FIG. 6D depicts an ESI-MS spectra of αGCN4 comprising a HC K129X and LC G202X mutation. X=pAcF.

FIG. 9A through FIG. 9C, depicts the results of exemplary experiments demonstrating site-specific conjugation of alkoxy-amine-derivatized monomethyl auristatin (MMAF) to αGCN4 Fab (LC-S155X/HC-K129X, X=pAcF). FIG. 9A depicts the results of exemplary experiments demonstrating the non-cleavable MMAF modified with a terminal alkoxy-amine was coupled by oxime ligation to antibody Fab fragment through para-acetyl phenylalanine (pAcF) residues. FIG. 9B depicts the results of exemplary experiments demonstrating ESI-MS characterization of the antibody Fab before conjugation. FIG. 9C depicts the results of exemplary experiments demonstrating ESI-MS analysis of the antibody Fab after conjugation and purification.

FIG. 10A depicts the results of exemplary experiments demonstrating in vitro cytotoxicity of αGCN4-Fab MMAF (LC-S155X, HC-K132X) towards the Ramos cancer cell line when mixed with or without αCD19-GCN4 fusions. FIG. 10B depicts the results of exemplary experiments demonstrating in vitro cytotoxicity of αGCN4-Fab MMAF (LC-S155X, HC-K132X) towards the SK-BR-3 cancer cell line when mixed with or without αHer2-GCN4 fusions. MMAF or GCN4-fused primary antibodies were also administered alone as controls.

FIG. 11A depicts the results of exemplary experiments demonstrating cytotoxicity on Ramos by anti-Her2 IgG (HC-GCN4 fusion) mixed with antiGCN4 Fab MMAF conjugates (LC-S155X/HC-K129X, X=pAcF), FIG. 11B depicts the results of exemplary experiments demonstrating cytotoxicity on SKBR3 by anti-CD19 IgG (HC-GCN4 fusion) mixed with anti-GCN4 Fab MMAF conjugates (LCS155X/HC-K129X, X=pAcF). Error bars represent SD of three replicates.

FIG. 12A through FIG. 12C, depicts the results of exemplary experiments demonstrating site-specific conjugation of alkoxy-amine-derivatized Alexa Fluor 488 (AF488) dye to αGCN4 Fab (LC-S155X/HC-K129X, X=pAcF). FIG. 12A depicts the results of exemplary experiments demonstrating the AF488 derivatized with a terminal alkoxy-amine was coupled through oxime ligation to pAcF residues on αGCN4 Fab. FIG. 12B depicts the results of exemplary experiments demonstrating ESI-MS characterization of the unconjugated αGCN4 Fab. FIG. 12C depicts the results of exemplary experiments demonstrating ESI-MS characterization of the AF488 conjugated Fab antibody.

FIG. 14A depicts the results of exemplary experiments demonstrating stepwise conjugation of αGCN4 Fab with alkoxy-amine-derivatized bicyclo[6.1.0] nonyne (BCN), followed by azide-derivatized Cy7. FIG. 14B depicts the results of exemplary experiments demonstrating ESI-MS characterization of the double conjugated αGCN4 Fab with BCN. FIG. 14C depicts the results of exemplary experiments demonstrating ESI-MS characterization of the purified final αGCN4 Fab conjugate with Cy7. FIG. 14D depicts the results of exemplary experiments demonstrating 10% SDS-PAGE characterization of αGCN4 site-specific conjugates. Lane 1: wt, Lane 2: double-αGCN4 Fab conjugate (LC-S155X/HC-K129X, X=pAcF) with MMAF toxin, Lane 3: double-αGCN4 Fab conjugate (LC-S155X/HC-K129X, X=pAcF) with Cy7.

FIG. 16A depicts the results of exemplary experiments demonstrating ex vivo near infrared fluorescence imaging of SKBR3 tumor xenografts. FIG. 16B depicts the results of exemplary experiments demonstrating ex vivo near infrared fluorescence imaging of Ramos tumor xenografts.

DETAILED DESCRIPTION

Figure 1:
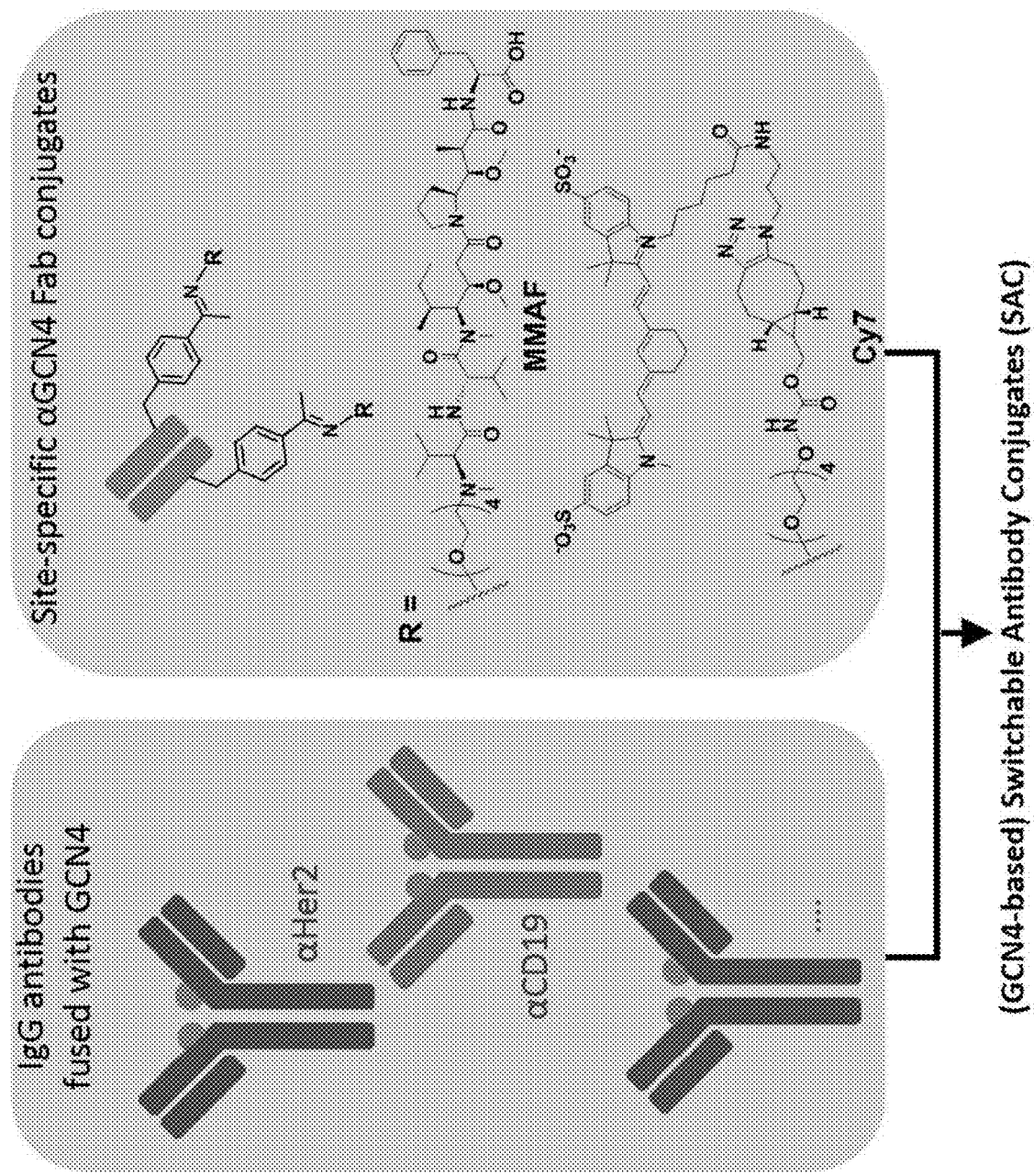
FIG. 1 depicts a schematic representation of the switch-mediated antibody conjugates (SAC).

In one embodiment, the present invention provides a system for generating site-specific conjugate molecules. In certain embodiments, the invention provides compositions for use in generating the site-specific conjugate molecules and compositions comprising the site-specific conjugate molecules. The site-specific conjugate molecules of the invention may be used for treating or preventing a disease or disorder in a subject.

In one embodiment, the system for generating site-specific conjugate molecules comprises an immunoconjugate molecule. In one embodiment, an immunoconjugate molecule comprises a polypeptide conjugated to at least one molecule. In one embodiment, the polypeptide of the immunoconjugate molecule comprises an antigen-binding domain, for example, a Fab fragment, which comprises an antigen binding domain which recognizes and binds to an antigen or epitope on a target molecule. In one embodiment, the polypeptide component of the immunoconjugate molecule comprises an anti-GCN4 Fab fragment. In one embodiment, the anti-GCN4 Fab fragment comprises a light chain sequence as set forth in SEQ ID NO:11 and a heavy chain sequence as set forth in SEQ ID NO:12.

In one embodiment, the polypeptide component of the immunoconjugate molecule comprises at least one amino acid modification. In one embodiment, the amino acid modification is distal to the antigen binding domain. In one embodiment, the amino acid modification is incorporation of an unnatural amino acid or a mutation of a natural amino acid (e.g., mutation to cysteine for thiol-mediated conjugation) which can be used for conjugation of at least one molecule to the polypeptide to form the immunoconjugate molecule.

In one embodiment, the at least one unnatural amino acid modification is at S193, S155 or G202 of the amino acid sequence as set forth in SEQ ID NO:11. In one embodiment, the at least one unnatural amino acid modification is at K129 or K132 of the amino acid sequence as set forth in SEQ ID NO:12. In one embodiment, at least one unnatural amino acid modification is p-acetylphenylalanine.

In one embodiment, incorporation of at least one amino acid modification is useful for conjugating at least one molecule to a polypeptide to form the immunoconjugate molecule. In one embodiment, a conjugated molecule is a chemical compound, a peptide, a protein, a detectable label or a nucleic acid molecule. In one embodiment, the conjugated molecule is a non-cleavable auristatin F (MMAF). In one embodiment, the conjugated molecule is alkoxy-amine-derivatized Alexa Fluor 488 (AF488). In one embodiment, the conjugated molecule is cyanine 7 (Cy7) dye.

In one embodiment, the immunoconjugate molecule comprises at least one, at least two, or more than two molecules conjugated to the heavy chain of a Fab fragment. In one embodiment, the immunoconjugate molecule comprises at least one, at least two, or more than two molecules conjugated to the light chain of a Fab fragment. In one embodiment, the immunoconjugate molecule comprises at least one, at least two, or more than two molecules conjugated to the heavy chain of a Fab fragment and at least one, at least two, or more than two molecules conjugated to the light chain of a Fab fragment.

In one embodiment, the system for generating site-specific conjugate molecules comprises at least one targeting molecule comprising a targeting domain for specifically binding to a target of interest and an immunoconjugate-antigen domain that serves as an antigen for recognition and binding by the immunoconjugate molecule. In one embodiment, the targeting molecule is an antibody containing a GCN4 peptide immunoconjugate-antigen domain. In one embodiment, the GCN4 peptide has a sequence as set forth in SEQ ID NO:2. In one embodiment, the GCN4 peptide is encoded by the nucleic acid sequence as set forth in SEQ ID NO:1. Therefore, in one embodiment, the invention relates to targeting molecules comprising SEQ ID NO:2 or nucleic acid sequences encoding the targeting molecules comprising SEQ ID NO:1.

In one embodiment, the targeting domain and the immunoconjugate-antigen domain are attached using a linker. A wide variety of linkers are known in the art that can be used in the attachment of a targeting domain and an immunoconjugate-antigen domain. In one embodiment, a linker is a G4S linker, having a sequence as set forth in SEQ ID NO:13. In one embodiment, a linker is a G35 linker.

In one embodiment, the targeting molecule is an antibody. In one embodiment, the antibody comprises a GCN4 peptide domain fused to the light chain of the antibody. In one embodiment, the antibody comprises a GCN4 peptide domain fused to the heavy chain of the antibody. In one embodiment, the targeting molecule is an anti-Her2 antibody having a light chain as set forth in SEQ ID NO:4, an anti-Her2 antibody comprising a heavy chain variable region as set forth in SEQ ID NO:6, an anti-CD19 antibody having a light chain as set forth in SEQ ID NO:8, or an anti-CD19 antibody having a heavy chain variable region as set forth in SEQ ID NO:10.

In one embodiment, the composition comprises a site-specific conjugate molecule comprising a targeting molecule-immunoconjugate fusion, wherein the antigen-binding domain of the immunoconjugate molecule is fused to the antigen domain of the targeting molecule. For example, in one embodiment, the anti-GCN4 Fab fragment of an anti-GCN4 Fab immunoconjugate molecule specifically recognizes and binds to a GCN4 peptide domain of an antibody of the invention, generating a site-specific conjugate molecule.

In certain embodiments, the present invention provides methods for detecting a target molecule in a sample using a site-specific conjugate molecule of the invention. In one embodiment, the method includes contacting a sample with a site-specific molecule of the invention wherein the site-specific molecule comprises a detectable label. In one embodiment, the detectable label is an imaging agent. In one embodiment, the detectable label is a dye belonging to Alexa Fluor series, or any other detectable label such as a fluorophore, a radioisotope label, or a magnetic resonance imaging (MRI) chelator. In one embodiment, the detectable label is Cy7.

In certain embodiments, the present invention provides methods for treating a disease or disorder in a subject comprising administering to the subject a site-specific conjugate molecule of the invention wherein the site-specific molecule comprises a therapeutic agent for the treatment of the disease or disorder. In one embodiment, the disease or disorder is cancer and the site-specific conjugate molecule of the invention comprises an anti-cancer therapeutic agent for the treatment of the cancer. In one embodiment, the cancer is breast cancer, and the method comprises administering to a subject in need thereof a site-specific conjugate molecule of the invention comprising an anti-Her2 antibody conjugated to an anti-cancer therapeutic agent. In one embodiment, the cancer is Ramos cancer, and the method comprises administering to a subject in need thereof a site-specific conjugate molecule of the invention comprising an anti-CD19 antibody conjugated to an anti-cancer therapeutic agent.

In one embodiment, the site-specific conjugate molecule of the invention is generated prior to administration to a subject. In an alternative embodiment, the targeting molecule and the immunoconjugate molecule of the invention are administered separately to a subject and the site-specific conjugate molecule of the invention is generated after administration. In one embodiment, the method comprises the steps of administering a targeting molecule to a subject as a pre-treatment followed by administration of an immunoconjugate molecule.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, "antigen-binding domain" means that part of the antibody, recombinant molecule, the fusion protein, or the immunoconjugate of the invention which recognizes the target or portions thereof.

As used herein, "aptamer" refers to a small molecule that can bind specifically to another molecule. Aptamers are typically either polynucleotide- or peptide-based molecules. A polynucleotide aptamer is a DNA or RNA molecule that adopts a highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that binds to specific ligands. Peptide aptamers may be identified and isolated from combinatorial libraries, using methods such as the yeast two-hybrid system.

The terms "biomarker" and "marker" are used herein interchangeably. They refer to a substance that is a distinctive indicator of a biological process, biological event and/or pathologic condition, disease or disorder.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.). The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The term "detecting" or "detection," means assessing the presence, absence, quantity or amount of a given substance (e.g., a DTC or DTC marker) within a clinical or subject-derived sample, including the derivation of qualitative or quantitative levels of such substances, or otherwise evaluating the values or categorization of a subject's clinical parameters.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein, "fragment" is defined as at least a portion of the variable region of the immunoglobulin molecule which binds to its target, i.e. the antigen binding region. Some of the constant region of the immunoglobulin may be included.

As used herein, "fused" means to couple directly or indirectly one molecule with another by whatever means, e.g., by covalent bonding, by non-covalent bonding, by ionic bonding, or by non-ionic bonding. Covalent bonding includes bonding by various linkers such as thioether linkers or thioester linkers. Direct fusion involves one molecule attached to the molecule of interest. Indirect fusion involves one molecule attached to another molecule which in turn is attached directly or indirectly to the molecule of interest.

As used herein, an "immunoconjugate" means any immunoglobulin molecule or fragment thereof such as an antibody or antibody fragment chemically or biologically linked to a cytotoxin, a radioactive agent, an anti-tumor drug or a therapeutic agent. The antibody or antibody fragment may be linked to the cytotoxin, radioactive agent, anti-tumor drug or therapeutic agent at any location along the molecule so long as it is able to bind its target. Examples of immuoconjugates include antibody conjugates and antibody fragment conjugates.

As used herein, "immunotoxin" means an antibody or antibody fragment chemically or biologically linked to a cytotoxin or cytotoxic agent.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprising amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "pharmaceutically acceptable carrier" includes any material which when combined with the antibody retains the antibody's immunogenicity and non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

By the term "specifically binds," as used herein, is meant a molecule, such as an antibody, which recognizes and binds to another molecule or feature, but does not substantially recognize or bind other molecules or features in a sample.

A "therapeutic" treatment is a treatment administered to a subject who exhibits signs of pathology, for the purpose of diminishing or eliminating those signs.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

As used herein, "tumor associated antigens" means any cell surface antigen which is generally associated with tumor cells, i.e., occurring to a greater extent as compared with normal cells. Such antigens may be tumor specific. Alternatively, such antigens may be found on the cell surface of both tumorigenic and non-tumorigenic cells. These antigens need not be tumor specific. However, they are generally more frequently associated with tumor cells than they are associated with normal cells.

As used herein, "tumor targeted antibody" means any antibody which recognizes cell surface antigens on tumor (i.e., cancer) cells. Although such antibodies need not be tumor specific, they are tumor selective, i.e., bind tumor cells more so than it does normal cells.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The invention provides compositions for use in generating site-specific conjugate molecules and methods of use for the treatment of diseases or disorders. In one embodiment, the invention provides a system for generating site-specific fusion molecules comprising 1) a targeting molecule which contains a domain for specific binding to a target of interest and a fusion epitope domain and 2) an immunoconjugate molecule which comprises a domain for specific recognition and binding to the fusion epitope domain of the targeting molecule.

Compositions

The present disclosure relates to compositions for use in a system for generating site-specific conjugate molecules. In various embodiments, the compositions of the invention include targeting molecules, immunoconjugate molecules, and site-specific conjugate molecules generated from the interaction of the targeting molecules and immunoconjugate molecules of the invention.

Immunoconjugate Molecules

In one embodiment, the invention provides immunoconjugate molecules. Immunoconjugate molecules of the invention comprise a polypeptide component comprising an antigen-binding domain, which recognizes a specific epitope or antigen of a targeting molecule, conjugated to one or more conjugate molecule.

The antigen-binding domain of the immunoconjugate, recognizes and specifically binds to an antigen, such as a protein, polypeptide, peptide, carbohydrate, polynucleotide, and lipid. In one embodiment, the polypeptide component of the immunoconjugate molecule may be an antibody fragment, including but not limited to Fab, Fab', F(ab')2, and Fv fragments. In one embodiment, the antigen-binding domain of the immunoconjugate molecule is specific for an epitope on the targeting molecule.

In one embodiment, the polypeptide component of the immunoconjugate molecule is conjugated to at least one molecule to form an immunoconjugate molecule. In one embodiment, the conjugation is random conjugation at one or more lysine residues. In one embodiment, the conjugation is site specific conjugation at one or more modified amino acid residue.

In one embodiment the polypeptide component of the immunoconjugate molecule is modified. Modifications that are contemplated for use in the immunoconjugate molecules of the invention include, but are not limited to disulfide bond formation, glycosylation, lipidation, acetylation, phosphorylation, or any other manipulation or modification, such as conjugation with a labeling component. Also included are, for example, mutation to cysteine for thiol-mediated conjugation or incorporation of one or more analogs of an amino acid (including, for example, unnatural amino acids, etc.) An "unnatural amino acid" is, in this case a molecule containing a primary amine functionality and carboxylic acid functionality that can be incorporated into a protein primary sequence with a transferable atom or group that is completely incorporated into the final product. In an embodiment, the unnatural amino acid is site-specifically incorporated into the immunoconjugate molecule. A general method of preparing a protein with a site-specifically incorporated unnatural amino acid is disclosed by Mehl et al., PCT/US2011/57043, and is incorporated herein by reference.

A very wide variety of non-naturally encoded amino acids are suitable for use in the present invention. Any number of non-naturally encoded amino acids can be introduced into the peptide if the invention. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a peptide of the invention that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

In some instances, the non-naturally encoded amino acids of the invention typically differ from the natural amino acids only in the structure of the side chain. The non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, alpha-hydroxy derivatives, gamma-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc.beta.-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, a p-propargyloxy-phenylalanine, a p-azido-L-phenylalanine (pAzF), a p-iodo-phenylalanine, a p-bromophenylalanine, a p-amino-L-phenylalanine and the like. In one embodiment, a non-naturally encoded amino acid for use in the invention is p-acetylphenylalanine (pAcF).

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}$H, $^{3}$H, $^{13}$C, $^{14}$C, 15N, $^{18}$O, $^{17}$O, $^{35}$S, $^{18}$F, $^{36}$Cl respectively. Certain isotopically-labelled compounds described herein, for example those into which radioactive isotopes such as $^{3}$H and $^{14}$C are incorporated, may be useful in drug and/or substrate tissue distribution assays. Further, substitution with isotopes such as deuterium, i.e., $^{2}$H, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In one embodiment, incorporation of at least one non-naturally encoded amino acid is beneficial for conjugating at least one molecule or moiety to a polypeptide comprising an antigen binding domain to form an immunoconjugate molecule. In one embodiment, the site-specific conjugates of the invention can be used for detection of a target or modifying a given biological response as well as for treatment of a disease or disorder. Therefore, the conjugated molecule or moiety is not to be construed as limited to any specific type of agent. Rather, any protein or polypeptide possessing a desired biological activity, a detectable molecule, cytotoxin, radioactive agent, anti-tumor drug or therapeutic agent may be conjugated to a polypeptide comprising an antigen binding domain to form an immunoconjugate molecule of the invention. Exemplary proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

The present invention may be used in connection with drugs of substantially all therapeutic classes including, for example, antibacterials, antivirals, antifungals, anticancer drugs, antimycoplasmals, and the like. The drug conjugates so constructed are effective for the usual purposes for which the corresponding drugs are effective.

Exemplary, non-limiting, molecules that can be incorporated into an immunoconjugate for use in the present invention include cytotoxic drugs, particularly those which are used for cancer therapy. Such drugs include, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. One skilled in the art may make chemical modifications to the desired compound in order to make reactions of that compound more convenient for purposes of preparing conjugates of the invention.

αGCN4 Fab Peptide

In one embodiment, the immunoconjugate molecule is an anti-GCN4 (αGCN4) Fab conjugate, wherein the polypeptide component comprises a modified αGCN4 Fab molecule. Therefore, in one embodiment, the invention includes αGCN4 Fab polypeptide molecules and nucleic acid molecules encoding the same for use in preparing the αGCN4 Fab conjugates of the invention. In one embodiment, the αGCN4 Fab polypeptide component comprises an immunoglobulin heavy chain having an amino acid sequence as set forth in SEQ ID NO:12. In one embodiment, the αGCN4 Fab polypeptide component comprises an immunoglobulin light chain having an amino acid sequence as set forth in SEQ ID NO:11. In one embodiment, the an αGCN4 Fab polypeptide component comprises an immunoglobulin heavy chain amino acid sequence having a sequence as set forth in SEQ ID NO:12 and a light chain amino acid sequence as set forth in SEQ ID NO:11.

In one embodiment, the αGCN4 Fab polypeptide component comprises at least one, at least two or more than two modifications. Modifications of the polypeptide component can be located at any amino acid residue so long as the modification does not interfere with the antigen recognition of the antigen binding domain (e.g., the modification is not in the Complementarity-determining regions (CDRs) of the Fab). In one embodiment, a modified αGCN4 Fab comprises at least one modification on an immunoglobulin light chain. In one embodiment, a modified αGCN4 Fab comprises at least one modification on an immunoglobulin heavy chain. In one embodiment, a modified αGCN4 Fab comprises at least one modification on an immunoglobulin light chain and at least one modification on an immunoglobulin heavy chain. In one embodiment, a modification on an immunoglobulin light chain is selected from a modification of S193, a modification of S155, and a modification of G202 of the amino acid sequence as set forth in SEQ ID NO:11. In one embodiment, a modification on an immunoglobulin heavy chain is selected from a modification of K129 and a modification of K132 of the amino acid sequence as set forth in SEQ ID NO:12.

In one embodiment the modification is incorporation of a non-naturally encoded amino acid. In one embodiment, the non-naturally encoded amino acid is pAcF. Therefore, in one embodiment the modification on an immunoglobulin light chain is selected from a modification of S193pAcF, a modification of S155pAcF, and a modification of G202pAcF of the amino acid sequence as set forth in SEQ ID NO:11. In one embodiment, the modification on an immunoglobulin heavy chain is selected from a modification of K129pAcF and a modification of K132pAcF of the amino acid sequence as set forth in SEQ ID NO:12. In one embodiment, incorporation of at least one non-naturally encoded amino acid is beneficial for use in conjugating at least one molecule to the modified αGCN4 Fab.

αGCN4 Fab Conjugates

In one embodiment, the modified αGCN4 Fab of the invention is conjugated to at least one molecule. In one embodiment, the heavy chain of the modified αGCN4 Fab is conjugated to a first molecule and the light chain of the modified αGCN4 Fab is conjugated to a second molecule. In various embodiments, at least one conjugated molecule may be a chemical compound, a peptide, a protein, a detectable label or a nucleic acid molecule. Exemplary conjugated molecules include, but are not limited to, non-cleavable auristatin F (MMAF), alkoxy-amine-derivatized Alexa Fluor 488 (AF488), and cyanine 7 (Cy7) dye, however, the invention is not limited to any class of compound or agent that can be conjugated to the modified αGCN4 Fab of the invention. Rather, any label, cytotoxin, radioactive agent, anti-tumor drug or therapeutic agent may be conjugated to a modified αGCN4 Fab of the invention.

Any appropriate method of conjugating molecules known in the art may be used to generate the αGCN4 Fab conjugates of the invention. The precise methods and reaction conditions used to prepare the αGCN4 Fab conjugates of the invention will depend upon the nature of the modification of the αGCN4 Fab and the nature of the molecule to be conjugated. For example, in one embodiment, conjugation of a molecule to a modified αGCN4 Fab of the invention comprising a pAcF may be achieved through the use of an alkoxy-amine derivatized PEG linker or oxime ligation. In an alternative embodiment, conjugation of a molecule to the modified αGCN4 Fab of the invention comprising a pAcF may achieved through. [3+2] click chemistry.

Targeting Molecule

In one embodiment, the invention provides targeting molecules comprising an immunoconjugate-antigen domain for recognition by and interaction with the immunoconjugate molecule of the invention and a targeting domain for specific binding to a target molecule of interest.

One skilled in the art understands that "targeting molecule" includes within its scope any molecule that specifically binds or reactively associates or complexes with a receptor or other receptive moiety associated with a given target cell population. This reactive molecule can be any molecule that binds to, complexes with or reacts with the cell population sought to be therapeutically or otherwise biologically modified. Such molecules include, but are not limited to, antibodies, proteins, aptamers, polypeptide or peptide ligands, and non-peptidyl ligands.

The targeting domain of the targeting molecule may be linked to the immunoconjugate-antigen domain directly or indirectly through a linker. The targeting molecule and the immunoconjugate-antigen domain can also be conjugated together through chemical conjugation. The immunoconjugate-antigen domain of the targeting molecule may be linked to the N-terminus or the C-terminus of the targeting domain, or may be incorporated internally into the targeting domain, for example, incorporated into the variable region of an antibody.

Antibodies

In one embodiment, the targeting molecule is an antibody that specifically binds to a target or protein of interest, sometimes referred herein as an antibody of the invention. Antibodies are capable of "specific binding" to a particular target or series of antigenically related targets. As used herein, an antibody is said to be capable of "specific binding" to an antigen if it discriminates from antigenically distinct molecules based on binding of those molecules to the variable region of the antibody. Such interactions are in contrast to non-specific binding that involve classes of compounds, irrespective of their chemical structure (such as the binding of proteins to nitrocellulose, etc.).

Such antibodies include polyclonal antibodies, monoclonal antibodies, Fab and single chain Fv (scFv) fragments thereof, bispecific antibodies, heteroconjugates, human and humanized antibodies. Such antibodies may be produced in a variety of ways, including hybridoma cultures, recombinant expression in bacteria or mammalian cell cultures, and recombinant expression in transgenic animals. The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species. Antibody fragments of small size, such as Fab and Fv fragments, having no effector functions and limited pharmacokinetic activity may be generated in a bacterial expression system. Single chain Fv fragments show low immunogenicity and are cleared rapidly from the blood.

The antibodies of the present invention may be polyclonal antibodies. Such polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include a positive or negative selection marker of the invention or a fragment thereof. Alternatively, a crude protein preparation which has been enriched for a positive or negative selection marker or a fragment thereof can be used to generate antibodies. Such proteins, fragments or preparations are introduced into the non-human mammal in the presence of an appropriate adjuvant. If the serum contains polyclonal antibodies to undesired epitopes, the polyclonal antibodies are purified by immunoaffinity chromatography.

Alternatively, the antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent, e.g. Kohler and Milstein, Nature 256:495 (1975). The immunizing agent will typically include a positive or negative selection marker or a fragment thereof and optionally a carrier. Alternatively, lymphocytes may be immunized in vitro. Generally, spleen cells or lymph node cells are used if non-human mammalian sources are desired, or peripheral blood lymphocytes ("PBLs") are used if cells of human origin are desired. The lymphocytes are fused with an immortalized cell line using a suitable fusing agent, such as polyethylene glycol, to produce a hybridoma cell. In general, immortalized cell lines are transformed mammalian cells, for example, myeloma cells of rat, mouse, bovine or human origin. The hybridoma cells are cultured in a suitable culture medium that preferably contains one or more substances that inhibit the growth or survival of unfused, immortalized cells. The culture medium (supernatant) in which the hybridoma cells are cultured can be assayed for the presence of monoclonal antibodies directed against a positive or negative selection marker by conventional techniques, such as by immunoprecipitation or by an in vitro binding assay, such as RIA or ELISA.

The monoclonal antibodies may also be made by recombinant DNA methods, such as those described in U.S. Pat. No. 4,816,567. DNA encoding the monoclonal antibodies of the invention can be isolated from the positive or negative selection marker specific hybridoma cells and sequenced, e.g., by using oligonucleotide probes that are capable of binding specifically to genes encoding the heavy and light chains of murine antibodies. Once isolated, the DNA may be inserted into an expression vector, which is then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for the murine heavy and light chain constant domains for the homologous human sequences, or by covalently joining to the immunoglobulin coding sequence all or part of the coding sequence for a non-immunoglobulin polypeptide. The non-immunoglobulin polypeptide can be substituted for the constant domains of an antibody of the invention, or can be substituted for the variable domains of one antigen-combining site of an antibody of the invention to create a chimeric bivalent antibody.

The antibodies may also be monovalent antibodies. Methods for preparing monovalent antibodies are well known in the art. For example, in vitro methods are suitable for preparing monovalent antibodies. Digestion of antibodies to produce fragments thereof, particularly, Fab fragments, can be accomplished using routine techniques known in the art.

Antibodies and antibody fragments characteristic of hybridomas of the invention can also be produced by recombinant means by extracting messenger RNA, constructing a cDNA library, and selecting clones which encode segments of the antibody molecule.

The antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', F(ab'), or other antigen-binding partial sequences of antibodies) which contain some portions of the sequence derived from non-human antibodies. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Methods for humanizing non-human antibodies are well known in the art. Generally, a humanized antibody has one or more amino acids introduced into it from a source which is non-human in order to more closely resemble a human antibody, while still retaining the original binding activity of the antibody.

Heteroconjugate antibodies which comprise two covalently joined antibodies, are also within the scope of the present invention. Heteroconjugate antibodies may be prepared in vitro using known methods in synthetic protein chemistry, including those involving crosslinking agents. For example, immunotoxins may be prepared using a disulfide exchange reaction or by forming a thioether bond.

In one embodiment, the antibodies of the invention are preferably specific for a target protein or peptide and so, do not bind peptides derived from other proteins with high affinity. In one embodiment, monoclonal antibodies, Fv fragments, Fab fragments, or other binding compositions derived from monoclonal antibodies of the invention have a high affinity to a cancer antigen. The affinity of monoclonal antibodies and related molecules to a cancer antigen may be measured by conventional techniques.

In one embodiment, the antibodies of the invention can be "chimeric antibodies" as that term is recognized in the art. As used herein, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L. et al., Proc. Nat'l Acad. Sci., 81, 6851 (1984).

Encompassed by the term "chimeric antibody" is the concept of "humanized antibody", that is those antibodies in which the framework or "complementarity" determining regions ("CDR") have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., L. Riechmann et al., Nature 332, 323 (1988); M. S. Neuberger et al., Nature 314, 268 (1985). Particularly preferred CDR'S correspond to those representing sequences recognizing the antigens noted above for the chimeric antibodies.

Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using crosslinking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

In one aspect, the antibodies of the present invention are useful for detecting, diagnosing, treating or preventing a disease or disorder associated with a targeted antigen. Such methods are advantageously applied to diagnosis and/or treat cancer. In one embodiment, antibodies of the invention can be used diagnostically to monitor protein levels in a sample as part of a clinical testing procedure, e.g., to determine the efficacy of a given treatment regimen. Detection can be facilitated by coupling (i.e., physically linking) the antibody to a label group.

In one embodiment, the antibodies mediate antibody-dependent cellular cytotoxicity, for example, the antibodies can kill antigen-positive cells. In one embodiment, an antigen-positive cell is a cancer cell. Therefore, in one embodiment, the antibody conjugates and recombinant immunotoxins are useful as reagents for killing tumor cells.

Aptamers

In one embodiment, the targeting molecule of the present invention is an aptamer. In one embodiment, the targeting molecule is a protein aptamer. In another embodiment, the targeting molecule is a polynucleotidal aptamer. In one embodiment, the aptamer of the invention is used to recognize and bind to at least one marker in a biological sample.

In one embodiment, an aptamer is a nucleic acid or oligonucleotide molecule that binds to a specific molecular target. In one embodiment, aptamers are obtained from an in vitro evolutionary process known as SELEX (Systematic Evolution of Ligands by EXponential Enrichment), which selects target-specific aptamer sequences from combinatorial libraries of single stranded oligonucleotide templates comprising randomized sequences. In some embodiments, aptamer compositions are double-stranded or single-stranded, and in various embodiments include deoxyribonucleotides, ribonucleotides, nucleotide derivatives, or other nucleotide-like molecules. In some embodiments, the nucleotide components of an aptamer include modified or non-natural nucleotides, for example nucleotides that have modified sugar groups (e.g., the 2'-OH group of a ribonucleotide is replaced by 2'-F or 2'-NH$_2$), which in some instances, improves a desired property, e.g., resistance to nucleases.

Modifications of the nucleic acids contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

In one embodiment, the selection of a nucleic acid ligand specific for a marker is carried out on a sensor chip surface and monitored by surface plasmon resonance. In one embodiment, aptamers are obtained from the screening of an RNA library. In one example, a combinatorial RNA library is made by transcribing DNA templates or a DNA library. However, in another embodiment, an aptamer is obtained from the screening of an ssDNA library (Chen et al., 2009, PLoS ONE, 4(12): e8142).

GCN4 Peptide Targeting Molecules

In one embodiment, the immunoconjugate-antigen domain of the targeting molecule of the invention comprises a GCN4 peptide which is recognized by the αGCN4 Fab conjugate of the invention. In one embodiment, the targeting molecule comprises or is linked to an amino acid sequence as set forth in SEQ ID NO:2. Exemplary targeting molecules of the invention include, but are not limited to, antibodies, peptides, proteins, aptamers, and nucleic acid molecules that are fused or linked, to a GCN4 peptide having an amino acid sequence as set forth in SEQ ID NO:2.

In one embodiment, the targeting molecule comprises an antibody wherein the GCN4 peptide is fused, linked or chemically conjugated, to the heavy chain or the light chain of the IgG. Exemplary antibodies of the invention, comprising a GCN4 peptide fusion, include an anti-Her2 antibody having a light chain as set forth in SEQ ID NO:4, an anti-Her2 antibody having a heavy chain (up to CH1) as set forth in SEQ ID NO:6, an anti-CD19 antibody having a light chain as set forth in SEQ ID NO:8, and an anti-CD19 antibody having a heavy chain (up to CH1) as set forth in SEQ ID NO:10. However, the invention should not be limited to these antibodies, as any antibody or molecule that includes a region for site-specific binding of an anti-GCN4-Fab conjugate (e.g., any antibody fused, linked or chemically conjugated to a peptide as set forth in SEQ ID NO:2) can be used as a targeting molecule in the invention.

Nucleic Acid

In one embodiment, the invention includes nucleic acid molecules encoding targeting molecules of the invention. The nucleic acid molecules may comprise any type of nucleic acid, including, but not limited to DNA and RNA. For example, in one embodiment, the composition comprises an isolated DNA molecule, including for example, an isolated cDNA molecule, encoding the targeting molecule. In one embodiment, the composition comprises an isolated RNA molecule encoding the targeting molecule.

The desired polynucleotide can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In one embodiment, the present invention provides a composition comprising an isolated nucleic acid encoding the targeting molecule of the invention, or a biologically functional derivative or analog thereof. In one embodiment, the isolated nucleic acid sequence comprises a sequence encoding the targeting domain operably linked to a sequence encoding an immunoconjugate-antigen domain of the targeting molecule, or a biologically functional derivative or analog thereof.

In one embodiment, the nucleic acid molecule comprises a nucleotide sequence encoding an amino acid sequence of SEQ ID NO:2 linked to an amino acid sequence of a targeting domain. In one embodiment, the nucleic acid molecule comprises a nucleotide sequence of SEQ ID NO:1 linked to a nucleotides sequence encoding a targeting domain.

Site-Specific Conjugates

In one embodiment, the compositions and systems of the invention are useful for generation of site-specific conjugates comprising an immunoconjugate-targeting molecule complex, wherein the immunoconjugate is fused to the targeting molecule through the interaction of the fusion epitope domain of the targeting molecule with the epitope recognition domain of the immunoconjugate molecule. In one embodiment, the site-specific conjugate of the invention may function as an immunotoxin, serving to deliver a cytotoxic drug or molecule to a specific target. In one embodiment, the immunotoxin is reactive with a desired target molecule expressed or present in a specific cell population. Neither the specific one cytotoxic molecule nor the specific target molecule is to be construed as a limitation on the present invention. The target molecules of the present invention may be used with any drug having a desired therapeutic, biological activity-modifying or prophylactic purpose.

Methods

In one embodiment, the invention relates to methods for detecting, diagnosing, preventing or treating a disease or disorder in a subject using the site-specific conjugated molecules of the invention.

In one embodiment, a disease or disorder is an infectious disease, including, but not limited to, a disease or disorder associated with a bacterial infection, a viral infection or a parasitic infection. Therefore, in one embodiment, the invention provides methods of detecting or treating an infectious disease or disorder in a subject in need thereof comprising administering to the subject a site-specific conjugated molecule wherein the molecule targets an antigen associated with an infectious agent.

In one embodiment, a disease or disorder is a disease associated with a self-antigen, including, but not limited to, an autoimmune disease. Therefore, in one embodiment, the invention provides methods of treating an autoimmune disease or disorder in a subject in need thereof comprising administering to the subject a site-specific conjugated molecule wherein the molecule targets a self-antigen associated with an autoimmune disease or disorder.

In one embodiment, a disease or disorder is cancer. The following are non-limiting examples of cancers that can be detected, diagnosed or treated by the disclosed methods and compositions: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and wilms tumor.

Therefore, in one embodiment, the invention provides methods of treating cancer in a subject in need thereof comprising administering to the subject a site-specific conjugated molecule wherein the molecule targets a cancer antigen.

Analysis Methods In some embodiments, the methods of the invention include performing an assay using a site-specific conjugated molecule of the invention. In one embodiment, the invention includes the use of a site-specific conjugated molecule in any bioassay that can be used to determine the level or concentration of at least one target protein or biomarker. For example, one or more site-specific conjugated molecule can be used to analyze and determine the presence or absence of at least one protein or biomarker in a sample. In one embodiment, a biological sample is contacted with one or more site-specific conjugated molecule to determine the concentration or level of expression of the at least one protein or biomarker in the sample. Immunoassay methods are suitable in this regard and may be carried out in any of a wide variety of formats. Immunological assay methods generally involve a reagent capable of specifically binding a marker. Suitable immunologic methods include, but are not limited to, immunoprecipitation, particle immunoassay, immunonephelometry, radioimmunoassay (RIA), enzyme immunoassay (EIA) including enzyme-linked immunosorbent assay (ELISA), sandwich, direct, indirect, or competitive ELISA assays, enzyme-linked immunospot assays (ELISPOT), multiplex ELISA array, fluorescent immunoassay (FIA), chemiluminescent immunoassay, flow cytometry assays, immunohistochemistry, Western blot, integrated blood barcode chip and protein-chip assays using for example the antibody or fragment thereof of the invention.

In one embodiment, once measured, the concentration of each biomarker and that of any other additional biomarker being assessed is compared to a predetermined reference value for the specific biomarker. The reference value may be determined in one of several ways. For example, the marker reference value can be the marker concentration measured in a sample taken from a control subject, or may be the median marker concentration calculated from the concentrations measured in multiple control samples taken from a group of control subjects.

Treatment Methods

In one embodiment, the invention provides a method of treating a disease or disorder in a subject in need thereof. In one embodiment, a disease or disorder is a malignancy or cancer. Therefore, in one embodiment, the invention provides methods of treating or preventing cancer, including, but not limited to treating or preventing proliferation, recurrence or metastasis of tumors in a subject in need thereof.

In some embodiments of the methods for treating or preventing cancer in an individual in need thereof, a site-specific conjugated molecule of the invention is administered to the individual. In some embodiments, the site-specific conjugated molecule comprises a cytotoxic molecule that is toxic to the targeted cancer cell.

The disclosed compounds can be used to prevent, abate, minimize, control, and/or lessen tumor growth, progression or metastasis in humans and animals. The disclosed compounds can also be used to slow the rate of primary tumor growth. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

In one embodiment, the invention provides methods for preventing metastasis of malignant tumors or other cancerous cells as well as to reduce the rate of tumor growth. The methods comprise administering an effective amount of a site-specific conjugated molecule of the invention to a subject diagnosed with a malignant tumor or cancerous cells or to a subject having a tumor or cancerous cells, wherein the site-specific conjugated molecule is targeted to a tumor antigen associated with the diagnosed cancer type. For example, in one embodiment, the cancer is breast cancer and the site-specific conjugated molecule is targeted to Her2.

In one embodiment, the invention further provides the administration of a site-specific conjugated molecule in combination with one or more additional therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

Other anti-tumor agents include cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. Small molecules, including topoisomerases such as razoxane, a topoisomerase II inhibitor with anti-angiogenic activity, can also be used.

Other anti-cancer agents that can be used include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The compositions of the invention may be administered to a patient or subject in need thereof in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease or disorder to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

In one embodiment, the methods include administration of the site-specific conjugate compositions to a subject in need thereof. Therefore, in one embodiment, a site-specific conjugate is generated prior to administration to a subject.

In an alternative embodiment, the methods include administration of the targeting molecule and the immunoconjugate molecule of the invention to a subject as separate compositions, wherein the targeting molecule and the immunoconjugate molecule generate a site-specific conjugate after administration to the subject. In such an embodiment, a composition comprising a targeting molecule of the invention may be administered at any appropriate time frame prior to or following administration of a composition comprising an immunoconjugate molecule of the invention. In one embodiment, a composition comprising a targeting molecule and a composition comprising an immunoconjugate molecule are administered substantially concurrently. In one embodiment, a composition comprising a targeting molecule is administered at least 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more than 24 hours prior to or following administration of a composition comprising an immunoconjugate molecule.

Kits

The present invention also pertains to kits useful in the methods of the invention. Such kits comprise various combinations of components useful in any of the methods described elsewhere herein, including for example, an immunoconjugate molecule, a targeting molecule, a site-specific conjugated molecule or any combination thereof. In one embodiment, the kit comprises an αGCN4 Fab conjugate, a GCN4 fusion targeting molecule, or a combination thereof. In one embodiment, the kit comprises other components e.g., control molecules and instructional material.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1: αGCN4-Fab Fragment Based Switchable Antibody System

Genetic incorporation of unnatural amino acids (UAAs) provide a unique approach to the synthesis of site-specific antibody conjugates that are homogeneous, better defined constructs than random conjugates and possess superior in vivo performance. Yet, optimization of site and yield is required for every single antibody, and the process is costly and time-consuming. The experiments presented herein demonstrate the development of a switchable antibody conjugate based on a αGCN4-Fab fragment that incorporated p-acetylphenylalanine at sites optimized for site-specific conjugation. A GCN4 peptide is used as a switch and antibodies readily fused by GCN4 can direct this αGCN4-Fab conjugate to target different cancer cells. When conjugated with auristatin-derived toxin, this site-specific antibody conjugate can be selectively cytotoxic to different cancer cells with single-digit nM $EC_{50}$s. When conjugated with imaging agents, the antibody conjugate can selectively detect and image different tumors in vitro and in vivo. More importantly, this GCN4-mediated antibody conjugate demonstrated an impressive potential for pretargeted imaging and therapy. This approach illustrates the utility of an orthogonal switch as a general and effective strategy to endow versatility to a single antibody conjugate, which should facilitate the application of UAA-based site-specific antibody conjugates for a host of therapeutic uses.

The materials and methods are now described.

Cloning of Antibody Expression Vector

Gene fragments encoding the variable regions of anti-Her2 (trastuzumab) (Wang et al., J Am Chem Soc 2015, 137 (9), 3229-3232) and anti-CD19 (FMC63) (Zola et al., Immunol Cell Biol 1991, 69 (Pt 6), 411-422) were synthesized by Integrated DNA Technologies (IDT) and amplified by PCR. The DNA sequence for GCN4 peptide is AATTATCATCTT-GAAAATGAGGTCGCTCGTCTCAAGAAACTC (SEQ ID NO:1) that codes for the amino acid sequence NYHLE-NEVARLKKL (SEQ ID NO:2). The DNA fragments encoding the constant regions of trastuzumab, along with the GGGGS (SEQ ID NO:13) linker that supports the GCN4 fusion were also synthesized by IDT and PCR amplified. Full length IgG heavy chains were constructed using the following mutations (E233P, L234V, L235A, ΔG236, A327G, A330S, and P331S) on Fc to reduce antibody-dependent cell-mediated cytotoxicity (ADCC) and complement-dependent cytotoxicity (CDC) (Wang et al., Proc Natl Acad Sci USA 2016, 113 (41), 11501-11506). These gene fragments were assembled using the Gibson Assembly kit (New England Biolabs) and subcloned into the pFuse backbone (Invivogen). Gene fragments encoding the variable regions of anti-GCN4 Fab were designed based on the sequences of the reported single chain antibody fragment (Zahnd et al., J. Biol. Chem. 2004, 279 (18), 18870-18877), synthesized by IDT, and assembled with the conserved constant regions of Fab heavy chain and lambda light chain. The final sequence was cloned into the pBAD backbone (Thermo Fisher). For unnatural amino acid incorporation, the desired sites were mutated to the TAG amber nonsense codon by QuickChange site-directed mutagenesis (Agilent). The sequences of the resulting expression vectors were confirmed by Sanger sequencing (GENEWIZ).

Expression and Purification of the Antibody Fusion Proteins

HEK293F cells (Life Technologies) were cultured in FreeStyle medium (Life Technologies), and were shaken at 37° C., 125 rpm, with 5% $CO_2$. The constructed pFuse vectors that contain the heavy chains and light chains of the GCN4 antibody fusions were co-transfected into HEK293F cells by transient transfection following the reported procedures (Wang et al., Proc Natl Acad Sci USA 2016, 113 (41), 11501-11506). The expression media containing the secreted antibodies were harvested every 48 hours after transfection and sterilized by filtration. The fusion antibodies were purified by Protein A chromatography (GenScript) and analyzed by SDS-PAGE and ESI-MS.

Expression and Purification of Antibody Fab Fragments

For wide type expression, pBAD vector that encodes αGCN4 Fab was transformed into TOP10 competent cells through electroporation (Bio-Rad Laboratories). The competent cells were recovered in SOC medium and plated onto a LB agar plate that contains ampicillin antibiotics. After overnight incubation at 37° C., the colonies showing up on the plate were picked, amplified, and mixed with 50% glycerol as a stock. The night before expression, 10 mL LB medium was supplemented with 100 μg/mL ampicillin, inoculated with the *E. coli* stock, and shaken at 37° C., 250 rpm (MaxQ 8000, Thermo Scientific). The next morning, the start culture was diluted into 1 L ampicillin-containing LB medium and continuously shaken at 37° C., 250 rpm. At $OD_{600}$ 0.8, protein expression was induced by 0.2% arabinose and the expression was continued for 24 hours at 30° C., 250 rpm (MaxQ 8000, Thermo Scientific). Cells were then harvested and the proteins were extracted by periplasmic lysis with 100 mL buffer (20% sucrose, 30 mM Tris (pH 8.0), 1 mM EDTA, and 0.2 mg/mL lysozyme). The extracts were separated from cell debris by centrifugation (9000 rpm for 40 min, Allegra, Beckman Coulter) and were sterilized through a 0.22 μm filtration. CH1 affinity column (CaptureSelect, Thermo Fisher) was used to purify the Fab protein. After loading the extracts, the affinity column was washed with 20 mL binding buffer (50 mM NaOAc, pH 5.2). The Fab fragments were then eluted out by 5 mL elution buffer (100 mM glycine, pH 2.8) and neutralized by 0.5 mL 1M Tris buffer. After buffer exchange with PBS buffer, the protein identity was analyzed by SDS-PAGE and ESI-MS.

For expression of Fab mutants, most procedures are the same as described above, except that pULTRA-pAcF (encodes orthogonal *Methanocaldococcus jannaschii* tRNA and aminoacyl-tRNA synthetase that are specific for incorporation of unnatural amino acid pAcF) vector was co-transformed with pBAD vector. Also, all the media should be added with both 100 μg/mL ampicillin and 100 μg/mL spectinomycin; and the expression media should have 1 mM pAcF unnatural amino acid. Once the $OD_{600}$ reaches 0.8, IPTG (1 mM final concentration) needs to be added in addition to arabinose to induce protein expression from the pULTRA plasmid.

ELISA Assay of αGCN4 Fab Fragments

The GCN4 peptide-fused αCD19 Fab (Rodgers et al., Proc. Natl. Acad. Sci. U.S.A 2016, 113 (4), E459-E468) (1 μg/mL, 100 μL/well) was coated onto a flat-bottom 96 well plate (black) over night to allow for attachment. After washing with PBS buffer (3 times), the wells were blocked with blocking buffer (PBS/1% BSA) at room temperature for 2 hours. Anti-GCN4 Fab fragments were serially diluted in blocking buffer and added into these wells in triplicate at a final volume of 100 μL/well. After an incubation of 2 hours, the wells were washed with PBS/0.05% Tween three times, followed by the addition of HRP-labelled anti-human lambda light chain antibody (Sigma Aldrich) that was 15,000 fold diluted in blocking buffer. After another 2 hour incubation, the wells were extensively washed by PBS/0.05% Tween five times. Finally, QuantaBlu fluorogenic ELISA substrate (Thermo Fisher) was added at 100 μL/well, and the fluorescence signals were developed and obtained through a Synergy H1 plate reader (BioTek). The data were processed and plotted via GraphPad Prism (GraphPad Software).

Conjugation and Purification of Fab Chemical Conjugates

Non-cleavable auristatin F (MMAF) with alkoxy-amine derivatized PEG linker was synthesized by Concortis Biotherapeutics (San Diego) based on published procedures (Axup et al., Proc Natl Acad Sci USA 2012, 109 (40), 16101-16106). αGCN4 Fab (HC-K129X, LC-S155X, X=pAcF) (1 mg, 21.6 nmol) was buffer exchanged by Amicon centrifugal filter (EMD Millipore) into 350 μL NaOAc buffer (50 mM, pH 4.2). MMAF-PEG-aminooxy linker (1.9 mg, 2.1 μmol) was then added to the antibody solution, and the reaction mixture was incubated at 37° C. for 24 hours. The extent of conjugation was monitored by ESI-MS, which showed >95% conversion efficiency within 24 hours. The antibody conjugate was purified by size exclusion column chromatography (Superdex 200, GE Healthcare) or Zeba spin desalting column (Thermo Fisher) based on the reported procedures (Wang et al., J Am Chem Soc 2015, 137 (9), 3229-3232; Wang et al., Proc Natl Acad Sci USA 2016, 113 (41), 11501-11506). The purity and the extent of labeling of the final conjugate were characterized by SDS-PAGE and ESI-qTOF protein MS.

The AF488 dye derivatized with a terminal alkoxy-amine was also conjugated to αGCN4 Fab (HC-K129X, LC-S155X, X=pAcF) by oxime ligation as described above.

For the conjugation of sulfo-Cy7 dye, bicyclo[6.1.0]nonyne (BCN) with an alkoxy-amine derivatized PEG linker (Kim et al., J Am Chem Soc 2012, 134 (24), 9918-9921) was first coupled to αGCN4 Fab (HC-K129X, LC-S155X, X=pAcF) through oxime ligation with the pAcF residues. When the reaction became complete within 24 hours, the antibody-BCN conjugate was purified by size filtration and the protein solution was buffer exchanged to PBS (pH 7.4). The concentration of αGCN4 Fab BCN conjugate was adjusted to 1 mg/mL (21 μM), followed by the addition of 0.17 mg/mL (210 μM) sulfo-cyanine 7 azide (Lumiprobe). The reaction mixture was incubated at 37° C. for 12 hours, at which time the conjugation was >95% complete as judged by ESI-MS. The double αGCN4 Fab conjugate with sulfo-Cy7 was purified and characterized following the aforementioned procedures.

In Vitro Cytotoxicity Assay

SK-BR-3 cell line (ATCC) was cultured and assayed in DMEM (Cellgro) supplemented with 10% (vol/vol) FBS, 100 IU/mL penicillin, and 100 μg/mL streptomycin. Ramos cell line (ATCC) was cultured and assayed in RPMI-1640 media mixed with the same supplements as described above. For cytotoxicity assay, SK-BR-3 cancer cells were plated in flat-bottom 96 well plates at 1000 cells, 90 μL fresh cell media/well, and were incubated overnight at 37° C., 5% $CO_2$. The MMAF compound and protein samples were filtered (0.22 μm, EMD Millipore), serially diluted in PBS buffer as 10× stock solutions, and added in triplicate to cancer cells (10 μL/well). To prevent evaporation, the edges of the plates were filled with 200 μL of bank media. The plates were then incubated at 37° C., 5% $CO_2$ for 72 hours, after which the ATP content of each well was measured by CellTiter Glo (Promega). The luminescence signals were detected on a Synergy H1 plate reader (BioTek). The viability of the cells treated with PBS buffer was used as a control, the signal of which was normalized as 100%. Ramos cancer cells were plated in flat-bottom 96 well plates at 10000 cells/well, and were directly treated with protein samples and MMAF control compound. The rest of the assay procedure was the same as described above.

Flow Cytometry Analysis

The breast cancer SK-BR-3 cell line and lymphoma Ramos cell line were harvested, washed with 4° C. PBS buffer, and finally fixed with 4% paraformaldehyde solution (ChemCruz) for 15 minutes. The cells were then washed with PBS, and blocked in Flow Cytometry Staining Buffer (Invitrogen) for 1 hour at the concentration of $1 \times 10^6$ cells/ mL. The GCN4-tagged primary IgG (αCD19 or αHer2 antibody) was mixed at room temperature with αGCN4 Fab (HC-K129X, LC-S155X, X=pAcF)-AF488 conjugate at the molar ratio of 1:2 for 2 hours, and then incubated with the fixed and blocked cancer cells at 4° C. for 1.5 hours. The cells were washed twice with cold PBS and analyzed on an LSR Fortessa flow cytometer (BD Biosciences). The results were processed with FlowJo software (TreeStar)

Animal Model

The animal experiments were in accordance with National Institute of Health guidelines and were conducted under the approval by University of Wisconsin Institutional Animal Care and Use Committee. Female athymic nude mice were used for subcutaneous SK-BR-3 tumor implantation while male CB17-SCID immunodeficient mice were used for subcutaneous Ramos tumor implantation. All mice were bought from Envigo (Indianapolis) at the age of 4 to 6 weeks old. On the day of tumor implantation, cancer cells were harvested and re-suspended in Matrigel (Invitrogen) at a concentration of $5\times10^6$ cells/mL. Around 200 μL of Ramos or SK-BR-3 cancer cells were subcutaneously injected into the lower right flank of each mouse. Mice were then continuously monitored for their health status and the tumor volumes were measured every other day.

In Vivo and Ex Vivo Near-Infrared Fluorescence Imaging of Tumors with αGCN4 Fab-Cy7 Conjugate In vivo near-infrared fluorescence (NIRF) imaging was performed on SK-BR-3 or Ramos mouse xenografts once the diameter of implanted tumor reached a length of 1 cm. The GCN4-tagged primary IgG (αCD19 or αHer2 antibody) was premixed with αGCN4 Fab (HC-K129X, LC-S155X, X=pAcF)-Cy7 at the molar ratio of 1:2 for 2 hours, and then injected intravenously into a group of mice (n=3) at a dosage of 60 primary IgG/mouse. At 1 hour, 4 hours, 8 hours, 16 hours, 24 hours, 48 hours, and 72 hours post injection, the mice were anesthetized with 2% isoflurane and placed on the stage of the IVIS Spectrum (PerkinElmer) with the tumor side facing the CCD camera. NIRF imaging was operated by Living Image 4.0 software, and was performed under the emission wavelength of 745 nm and exciting wavelength of 800 nm. Automatic scanning time was used to prevent image saturation. Regions of interests (ROIs) were placed on the 2D NIRF image to encompass the entire NIRF signal. The mice were finally euthanized, with major organs, tissues, and tumors collected and imaged Ex vivo following the same protocol as described above.

In Vivo and Ex Vivo Near-Infrared Fluorescence Imaging of Pre-Targeting Antibodies with αGCN4 Fab-Cy7 Conjugate For pre-targeting, GCN4-tagged primary IgG (αCD19 or αHer2 antibody) was injected intravenously into SK-BR-3 orthotopic xenograft mouse model at a dosage of 60 μg antibody/mouse. At 4 hours post injection of the primary antibody, αGCN4 Fab-Cy7 conjugate was injected intravenously as well, at a dosage of 35 μg/mouse. As a control group, mice were injected with PBS buffer, followed by αGCN4 Fab-Cy7 conjugate at 4 hours post the initial injection of PBS. Subsequent NIRF imaging was performed up to 48 hours using the IVIS Spectrum (PerkinElmer), and followed the same procedures as described above for tumor imaging.

The results are now described.

Figure 2:
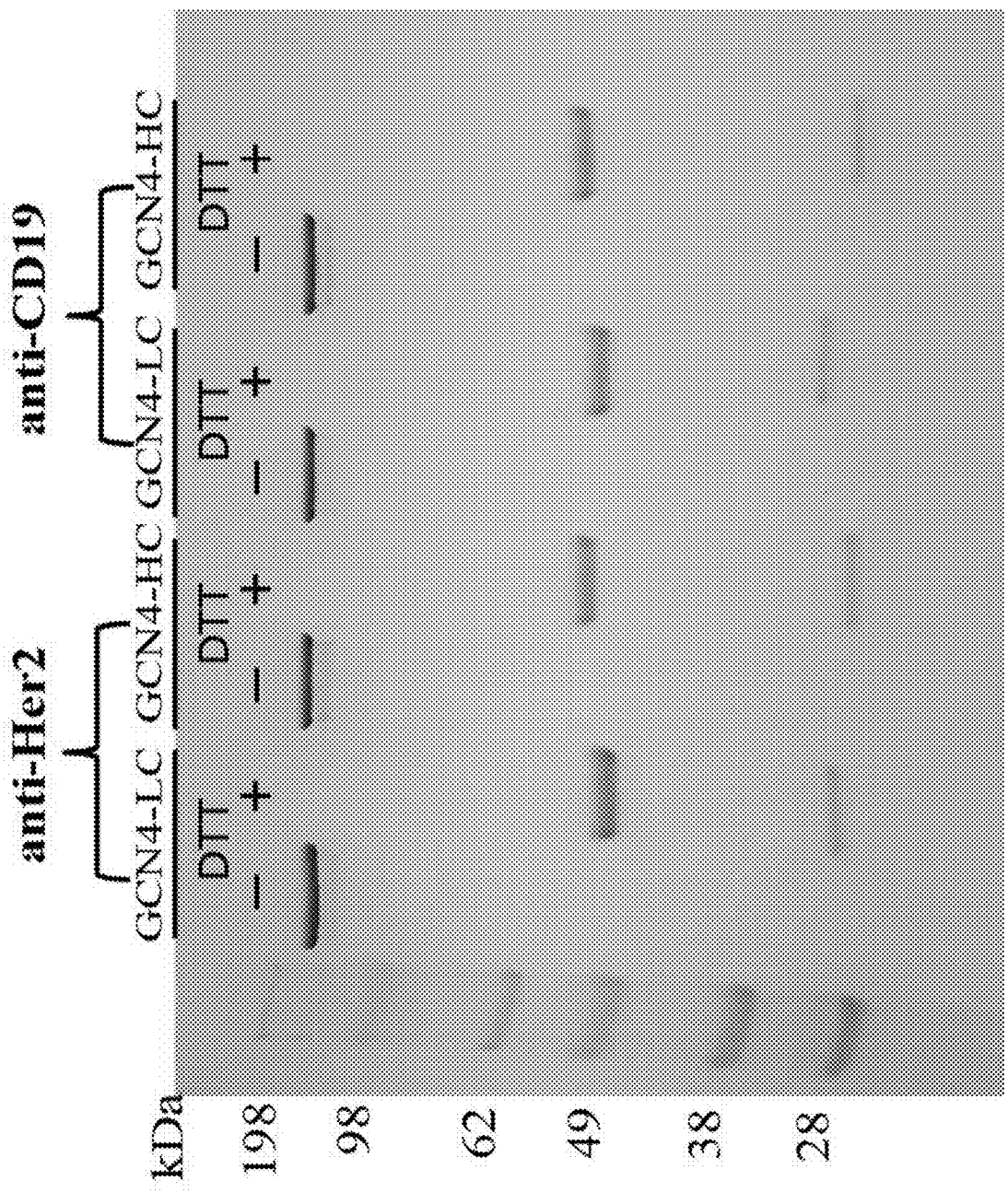
FIG. 2 depicts the results of exemplary experiments demonstrating SDS-PAGE analysis of GCN4 fusion antibodies (anti-Her2 and anti-CD19).
Figures 4A, 4B:
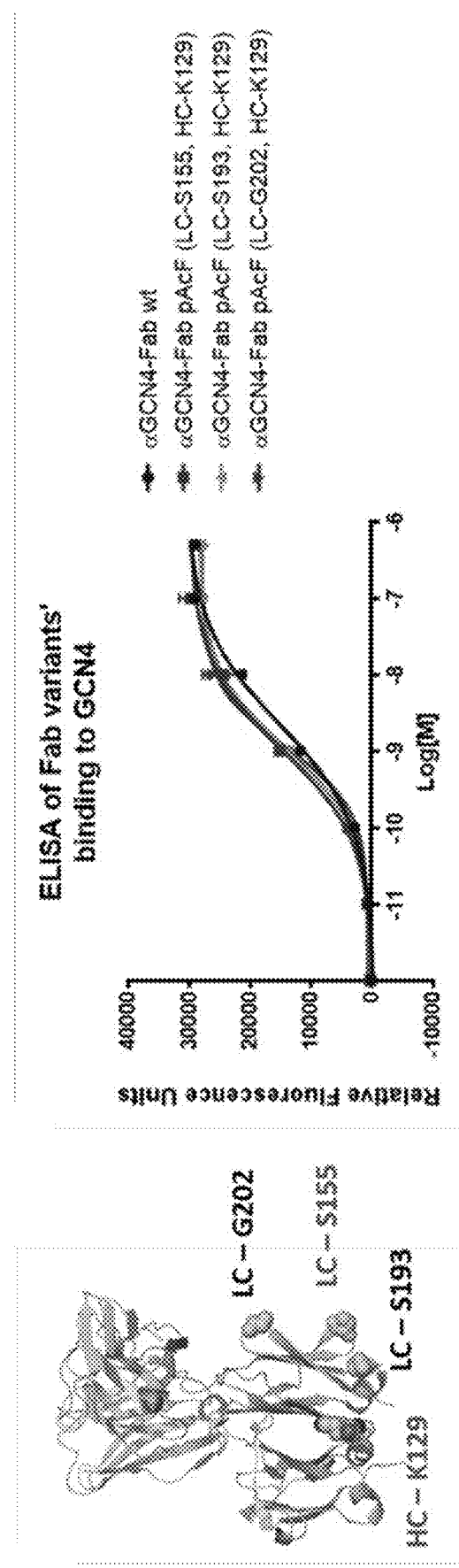
FIG. 4A through FIG. 4B, depicts the results of exemplary experiments demonstrating the generation of αGCN4 mutants.

Recently, a 14-mer peptide sequence from the yeast transcription factor GCN4 was fused to antibodies, thereby directing the targeting of GCN4-selective CAR-T cells to CD19- or CD20-positive tumor cells (Rodgers et al., Proc. Natl. Acad. Sci. U.S.A. 2016, 113 (4), E459-E468). The fact that this 'GCN4 tag' has a low probability of immunogenicity, satisfactory in vivo stability, and is orthogonal to human proteins (Rodgers et al., Proc. Natl. Acad. Sci. U.S.A 2016, 113 (4), E459-E468) suggests that it may be usable as a switch to mediate the targeting of GCN4-selective antibody conjugates (FIG. 1). Primary IgGs could be readily fused with the GCN4 peptide in order to direct αGCN4 antibody conjugates towards their cognate antigens on tumor surfaces. For proof of concept, traztuzumab was picked to target Her2-positive breast cancer (Lewis Phillips et al., Cancer Res. 2008, 68 (22), 9280-9290) and FMC63 to target αCD19-positive B-cell lymphoma (Du et al., Cancer Res. 2008, 68 (15), 6300-6305), both of which are popular targets for immunotherapy. The 14-mer sequence from GCN4 was inserted into the loop of the antibody to replace Lys169 at the CL constant region of the light chain or Ser180-Gly181 at the CH1 constant region of the heavy chain, following the reported procedures for direct peptide-antibody loop fusion (Wang et al., J. Am. Chem. Soc. 2015, 137 (9), 3229-3232; Rodgers et al., Proc. Natl. Acad. Sci. U.S.A 2016, 113 (4), E459-E468; Wang et al., Proc. Natl. Acad. Sci. U.S.A 2016, 113 (41), 11501-11506). The peptide was flanked with $(Gly)_4$Ser linker to afford the desired flexibility. The resulting fusion constructs were expressed in HEK293F cells by transient transfection, with yields of more than 10 mg/L after column purification. SDS/PAGE analysis revealed that all four fusion antibodies migrated as a single band, with >95% purity and a molecular mass of ~165 kDa (FIG. 2). After DTT reduction, the light chains migrated close to ~25 kDa, whereas the heavy chains migrated at ~50 kDa, matching the expected molecular weights. Their identities were further confirmed by ESI-MS analysis (FIG. 3).

Among all the available scaffolds that can be used to create an αGCN4 antibody, Fab fragments are of interest due to their much shorter circulation half-lives than a full-length IgG, which makes them less likely incur off-target-related systematic toxicity for therapeutic treatment or background signals for imaging diagnosis. Compared to other small sized antibody fragments, Fab still has constant regions that are distal to antigen-binding sites to allow for point mutation and conjugation. Based on the sequence of an αGCN4 single-chain variable fragment (ScFv) that has a binding affinity of about 5 pM (Zahnd et al., J. Biol. Chem. 2004, 279 (18), 18870-18877), a plasmid was constructed (pBAD αGCN4) harboring the heavy- and lambda light-chain genes of the Fab fragment following an stII signal peptide (Kim et al., Proc. Natl. Acad. Sci. U.S.A 2013, 110 (44), 17796-17801). The wild type αGCN4 Fab was expressed in E. coli by shake flask, yielding 7.4 mg/L after purification.

Figure 5:
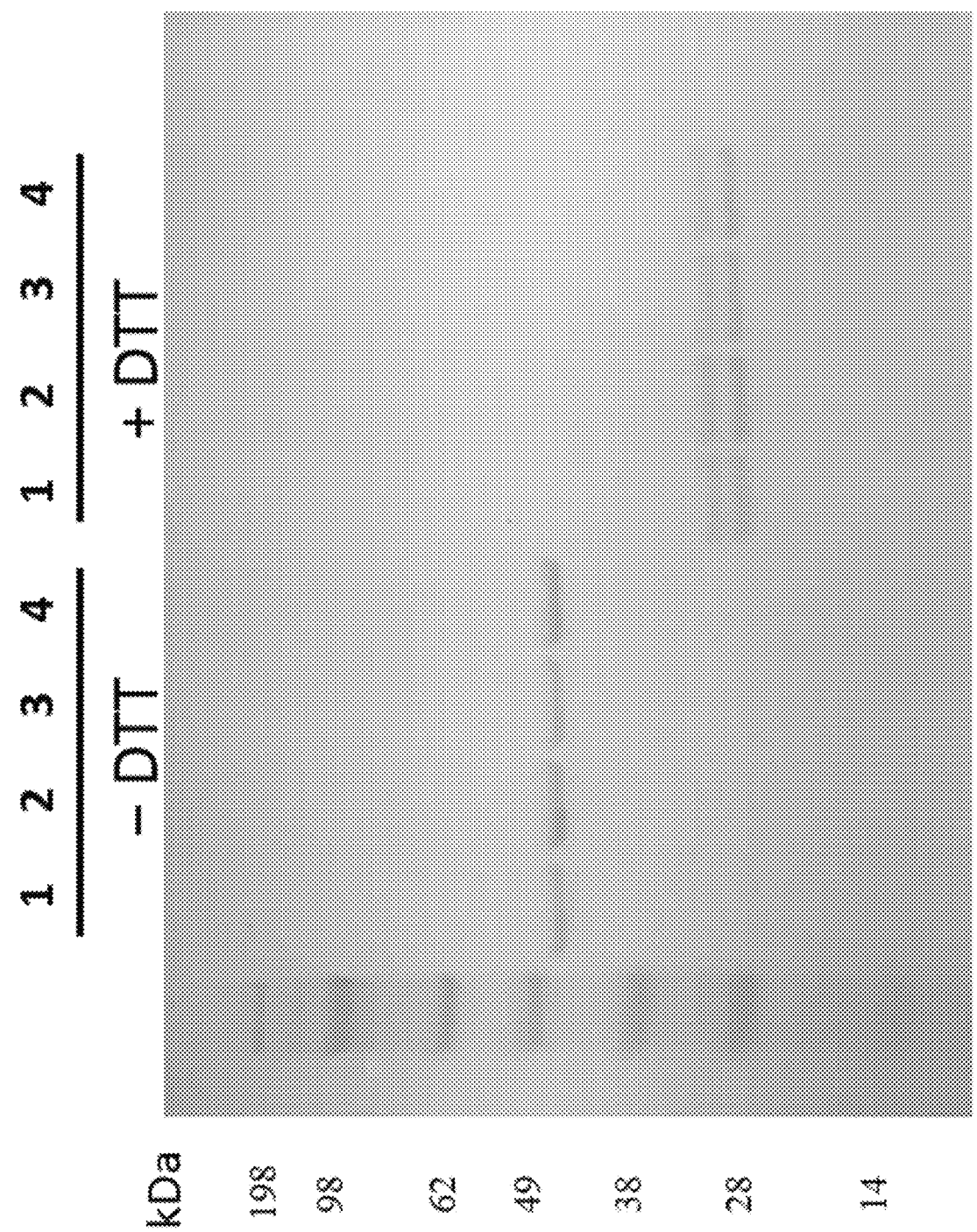
FIG. 5 depicts the results of exemplary experiments demonstrating SDS-PAGE characterization of αGCN4-Fab antibodies. Lane 1, wild type; Lane 2, HC-K129X, LC-S155X double mutated; Lane 3, HC-K129X, LC-S193X double mutated; Lane 4, HC-K129X, LC-G202X double mutated. X=pAcF.
Figure 6C:
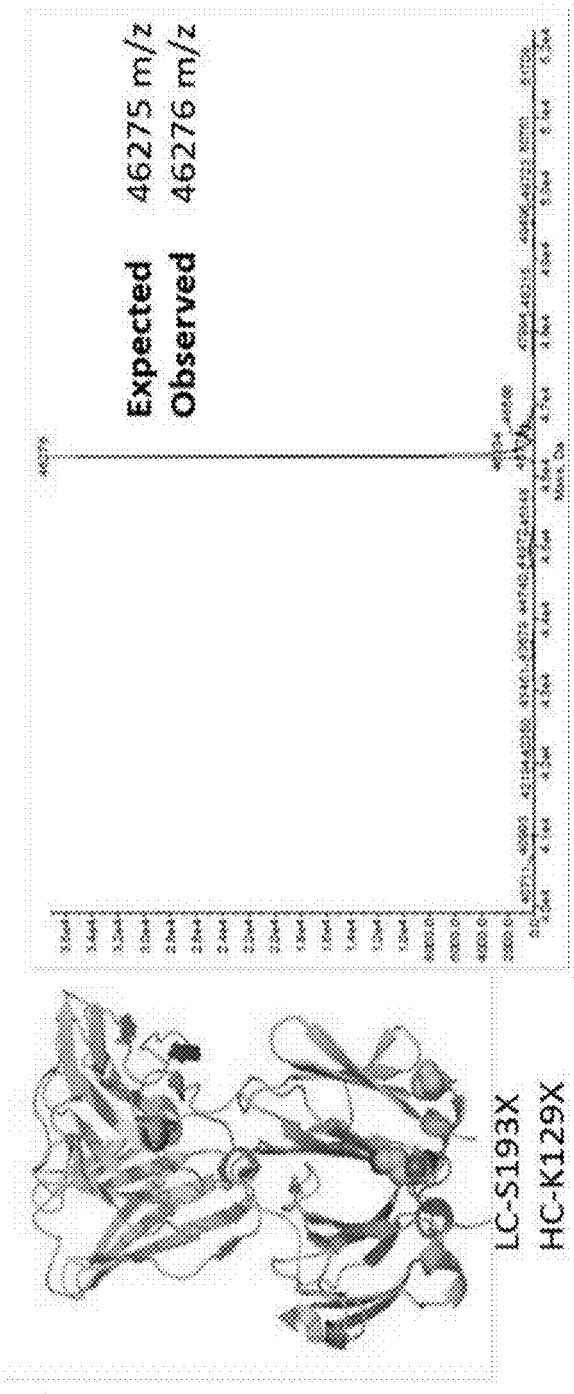
Figure 6D:
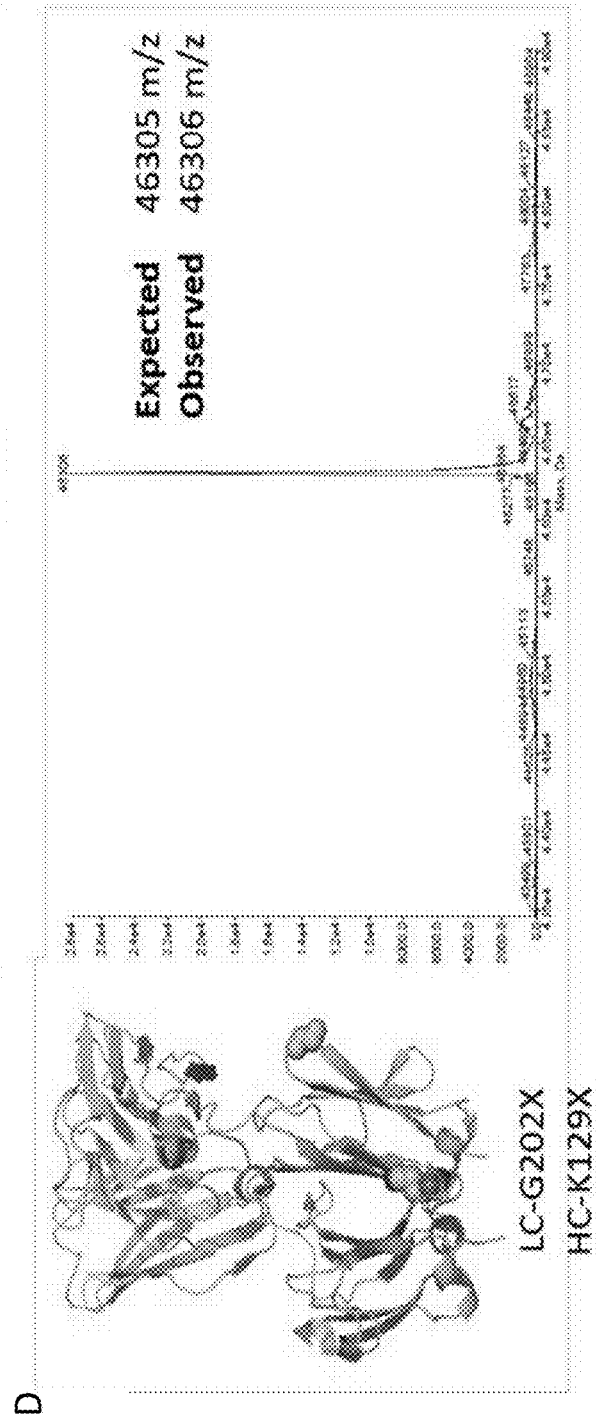

The genetic incorporation of UAAs such as pAcF not only allows site-specific modification of the protein surface but also facilitates the exploration of various Fab conjugates with different geometries and stabilities (Kim et al., Proc. Natl. Acad. Sci. U.S.A 2013, 110 (44), 17796-17801). For example, previous studies on a Fab fragment bearing a kappa light chain revealed solvent-exposed sites such as HC-K129 that has a high expression yield and coupling efficiency, as well as little interference with antigen-binding (Axup et al., Proc. Natl. Acad. Sci. U.S.A 2012, 109 (40), 16101-16106; Kim et al., Proc. Natl. Acad. Sci. U.S.A 2013, 110 (44), 17796-17801). Nonetheless, mutation site on the lambda light chain has not been explored yet. In a search for an optimal conjugation site, three additional sites (LC-S155X, LC-S193X, LC-G202X) were selected on the lambda light chain of αGCN4, which are surface-exposed, in flexible loops, and distal to binding sites (FIG. 13A). Briefly, the pBAD plasmid that encodes the αGCN4 Fab with double mutations to TAG codon on HC-K129X, and one of the sites from LC-5155X, LC-5193X, or LC-G202X was co-transformed into DH10B strain with a plasmid (pUltrapAcF) that encodes the Mj-tRNA/tyrosyl-tRNA synthetase pair evolved to incorporate the pAcF UAA22. The shake-flask expression yield for αGCN4-Fab (LC-5155X, HC-K129X, X=pAcF) was 3.4 mg/L, while the yields for αGCN4-Fab (LC-S193X, HC-K129X, X=pAcF) and αGCN4-Fab (LC-G202X, HC-K129X, X=pAcF) were 0.68 mg/L and 0.34 mg/L, respectively. The varying yields for these Fab mutants confirmed that antibody stability depends on the site of mutation, which may also suggest that the closer the amber suppression is towards the N-terminus, the more stable the mutant is. Nevertheless, all the aforementioned αGCN4 Fab antibodies migrated as a single band on SDS/PAGE analysis, with >95% purity and a molecular mass of ~46 kDa (FIG. 5). Follow-up ESI-MS analysis further confirmed their identities, with the results correlating well to the theoretical molecular weights (FIG. 6). The affinity of these mutants was assessed through an ELISA assay. As shown in FIG. 13B, the mutated αGCN4 Fab fragments have an affinity indistinguishable from the wild-type Fab, with a half-maximal binding constant ($EC_{50}$) of ~1 nM. αGCN4-Fab (LC-S155X, HC-K129X, X=pAcF) was selected for following-up experiments, based on the expression yield.

Figure 7:
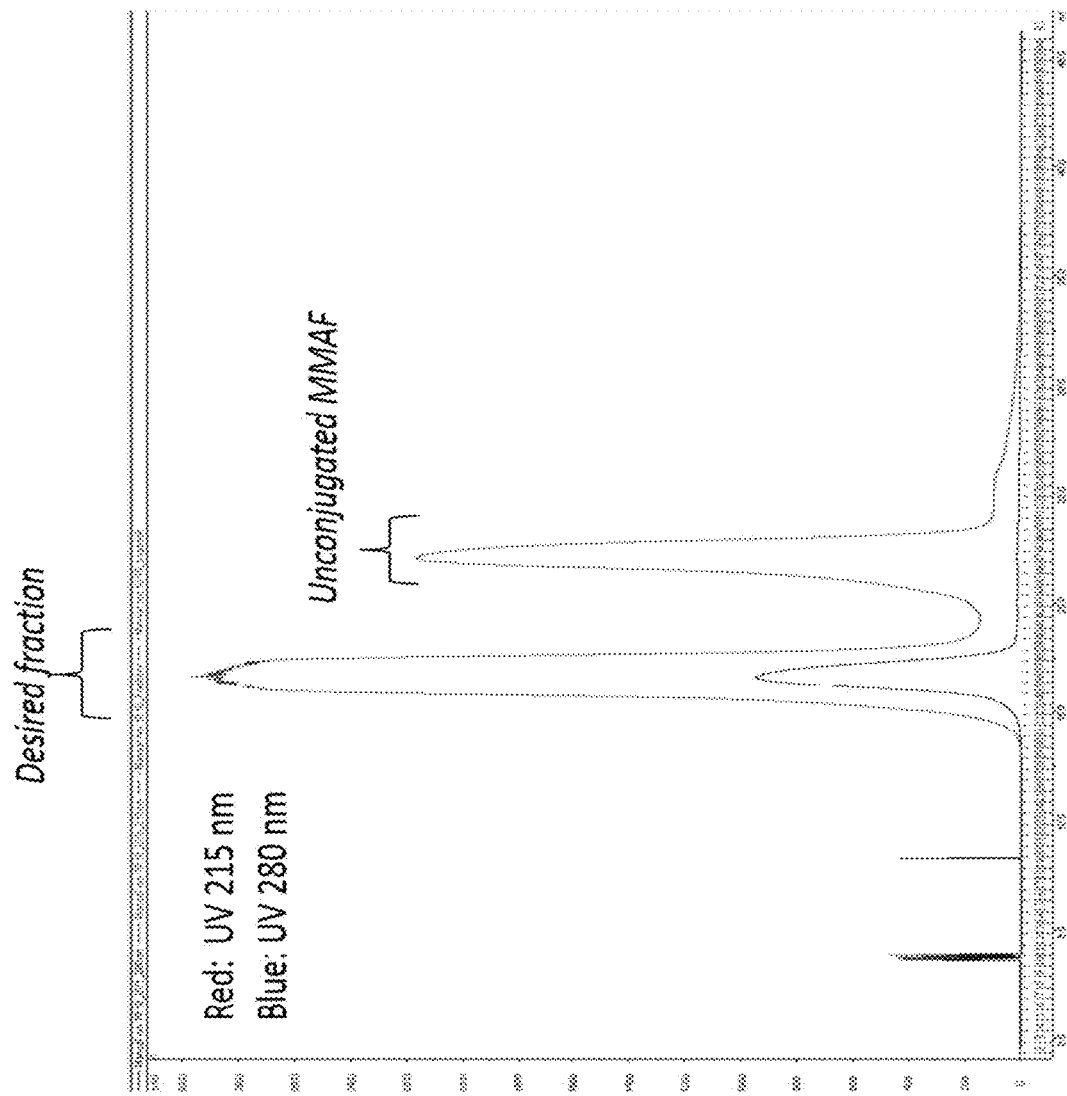
FIG. 7 depicts the results of exemplary experiments demonstrating size exclusion chromatography FPLC trace for the purification of double αGCN4 Fab conjugates (LC-S155X/HC-K129X, X=pAcF) with monomethyl auristatin F (MMAF).
Figure 10A:
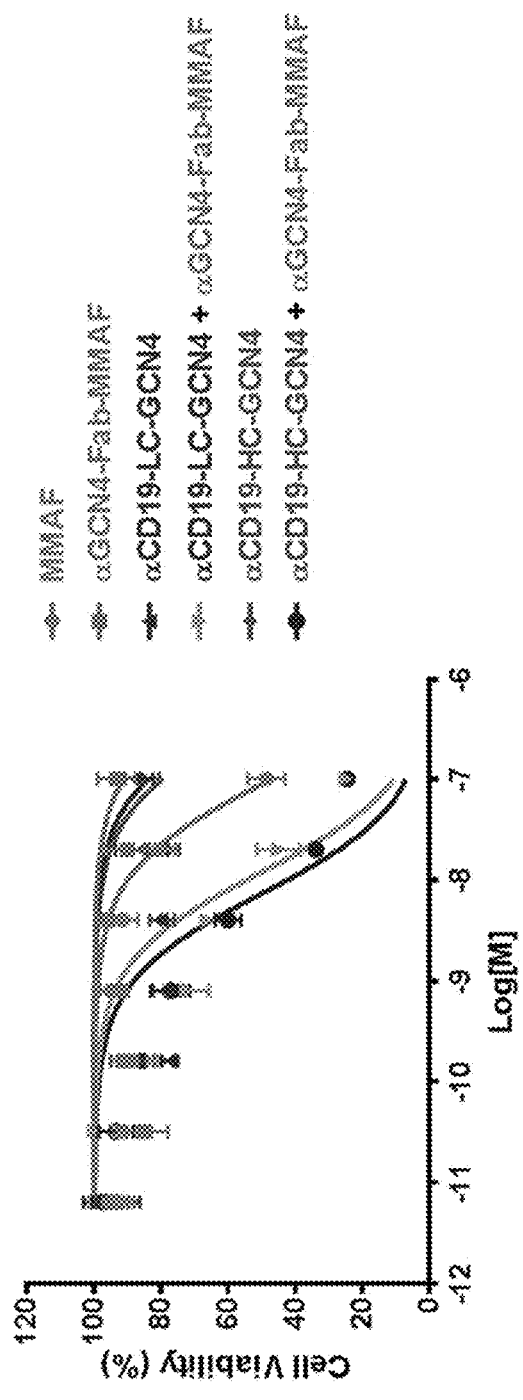
FIG. 10A through FIG. 10B, depicts the results of exemplary experiments demonstrating in vitro cytotoxicity of αGCN4-Fab MMAF (LC-S155X, HC-K132X) towards cancer cell lines when mixed with or without αCD19-GCN4 fusions.
Figure 10B:
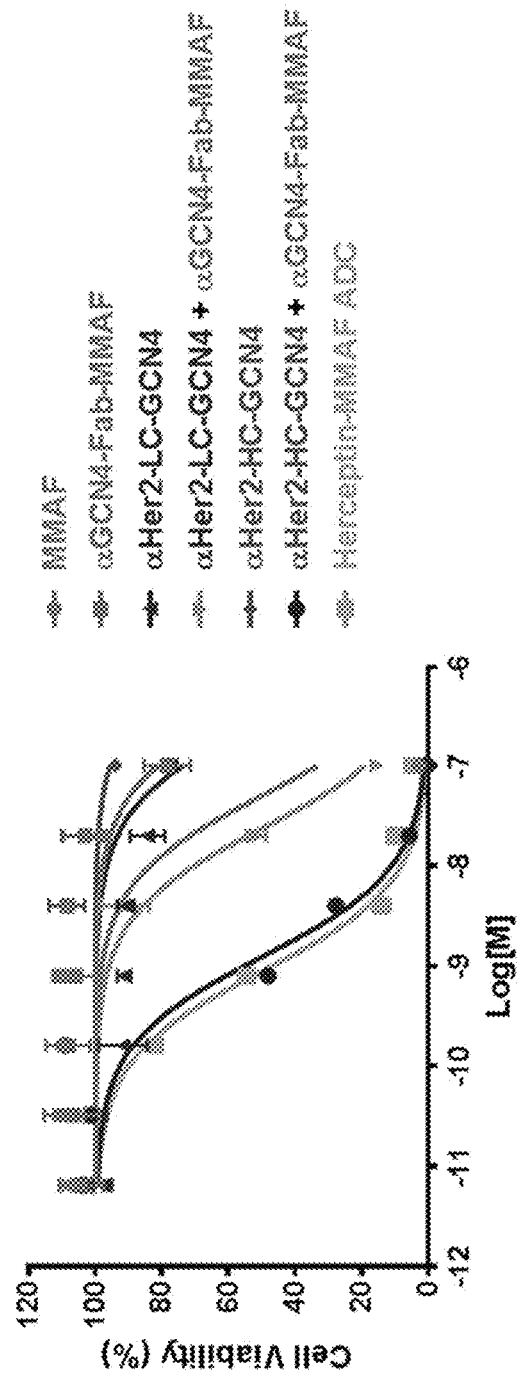
Figure 11A:
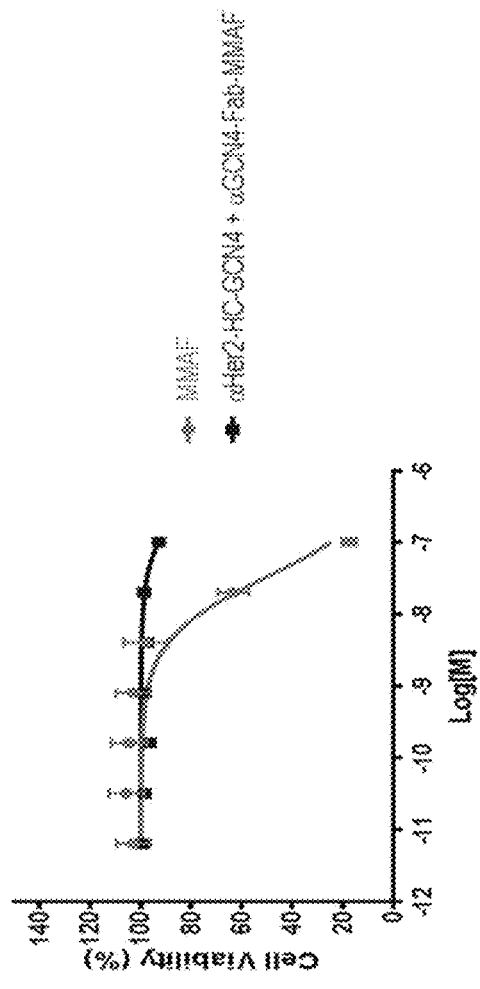
FIG. 11A through FIG. 11B, depicts the results of exemplary experiments demonstrating an in vitro cell cytotoxicity assay to confirm the specificity of switchable antibody drug conjugates.
Figure 11B:
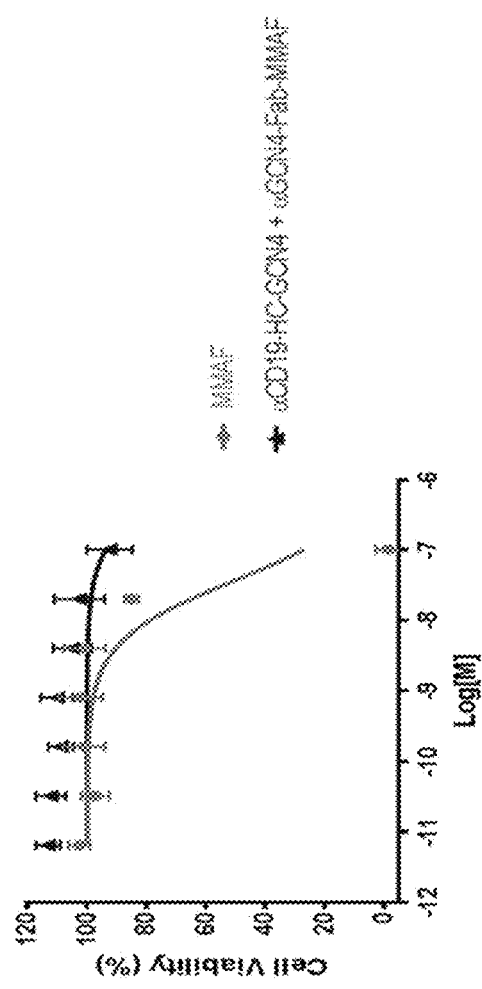

To utilize GCN4 as a switch for the treatment of different cancers, a site-specific αGCN4-based ADC was synthesized by conjugating αGCN4-Fab (LC-S155X, HC-K129X, X=pAcF) with a non-cleavable auristatin F linker compound (MMAF) (Axup et al., Proc. Natl. Acad. Sci. U.S.A 2012, 109 (40), 16101-16106; Kularatne et al., Angew. Chem. Int. Ed. Engl. 2014, 53 (44), 11863-11867) (FIG. 1). The pAcF-containing αGCN4-Fab was reacted with a 100-fold excess of aminooxy-derived MMAF at 37° C. for 24 hours, and purified by size-exclusion chromatography (FIG. 7). Both SDS/PAGE (FIG. 8) and ESI-MS analysis (FIG. 9) showed that the final αGCN4 ADC is >95% pure, and has the desired molecular weight with a drug-to-antibody ratio (DAR) of 2 (FIG. 9). The in vitro cytotoxicity of the αGCN4-Fab-MMAF conjugate and/or GCN4-tagged primary IgGs was evaluated at the end of their 72 hour incubation with a CD19-positive Burkitt's lymphoma cell line Ramos or a Her2-positive breast cancer cell line SK-BR-3 (FIG. 10). The MMAF compound was used as a positive control and displayed medium cytotoxicity ($EC_{50}$s~50-89 nM, Table 1) due to its limited cell permeability (Kularatne et al., Angew. Chem. Int. Ed. Engl. 2014, 53 (44), 11863-11867). When mixed with αCD19-GCN4 fusions at a molar ratio of 2:1, αGCN4-Fab-MMAF showed significant toxicity towards Ramos cell line ($EC_{50}$=12±7 nM with αCD19-LC-GCN4; $EC_{50}$=7±4 nM with αCD19-HC-GCN4) (FIG. 10A, Table 1). Similarly, the mixture of αGCN4-Fab-MMAF and αHer2-GCN4 fusions potently killed SK-BR-3 breast cancer cells ($EC_{50}$=23±11 nM with αHer2-LC-GCN4; $EC_{50}$=1.2±0.6 nM with αHer2-HC-GCN4) (FIG. 10B, Table 1). The fact that the GCN4 peptide fused at the heavy chain (CH1) of the primary IgG led to more significant cytotoxicity compared to fusion at the light chain (CL) suggests that there could be more space surrounding the CH1 region for binding by αGCN4-Fab. Protein binding to the CH1 region may also interference less with the primary IgG's interaction with antigens and their follow-up internalization. Although it still awaits for validation with more cases, this pattern could possibly guide future antibody tagging with the GCN4 peptide. Notably, the most potent mixture (αHer2-HC-GCN4: αGCN4-Fab-MMAF) is similar in efficacy to that of the previously reported Herceptin-MMAF conjugate ($EC_{50}$=0.9±0.2 nM) (FIG. 10B, Table 1). On the other hand, the αGCN4-Fab-MMAF conjugate or any of the GCN4-tagged primary antibodies when administered alone turned out ineffective towards either cancer cell line ($EC_{50}$s>100 nM), indicating that the cytotoxic effects require the activation of αGCN4-based ADC by GCN4. To examine the selectivity of GCN4-mediated ADCs, the cytotoxicity of αHer2-HC-GCN4: αGCN4-Fab-MMAF was tested on Ramos cells that are Her2-negative (FIG. 11A), and the cytotoxicity of αCD19-HC-GCN4: αGCN4-Fab-MMAF was tested on SK-BR-3 cells that are CD19-negative (FIG. 11B). In both cases, the combination failed to show any activity ($EC_{50}$>100 nM) while the MMAF small molecule control worked well. Taken together, these results demonstrate that with a GCN4 switch, the site-specific αGCN4-Fab-MMAF conjugate can be directed by primary antibodies to selectively and potently inhibit different tumor cells.

TABLE 1

| Construct | $EC_{50}$ (nM) on SK-BR-3 | $EC_{50}$ (nM) on Ramos |
|---|---|---|
| MMAF | 50 ± 39 | 89 ± 37 |
| αGCN4-Fab | >100 | >100 |
| αCD19-LC-GCN4 | N.D. | >100 |
| αCD19-HC-GCN4 | N.D. | >100 |
| αHer2-LC-GCN4 | >100 | N.D. |
| αHer2-HC-GCN4 | >100 | N.D. |
| αCD19-LC-GCN4/ αGCN4-Fab-MMAF | N.D. | 12 ± 7 |
| αCD19-HC-GCN4/ αGCN4-Fab-MMAF | >100 | 7 ± 4 |
| αHer2-LC-GCN4/ αGCN4-Fab-MMAF | 23 ± 11 | N.D. |
| αHer2-HC-GCN4/ αGCN4-Fab-MMAF | 1.2 ± 0.6 | >100 |

N.D. indicates the activity was not determined.

Figure 8:
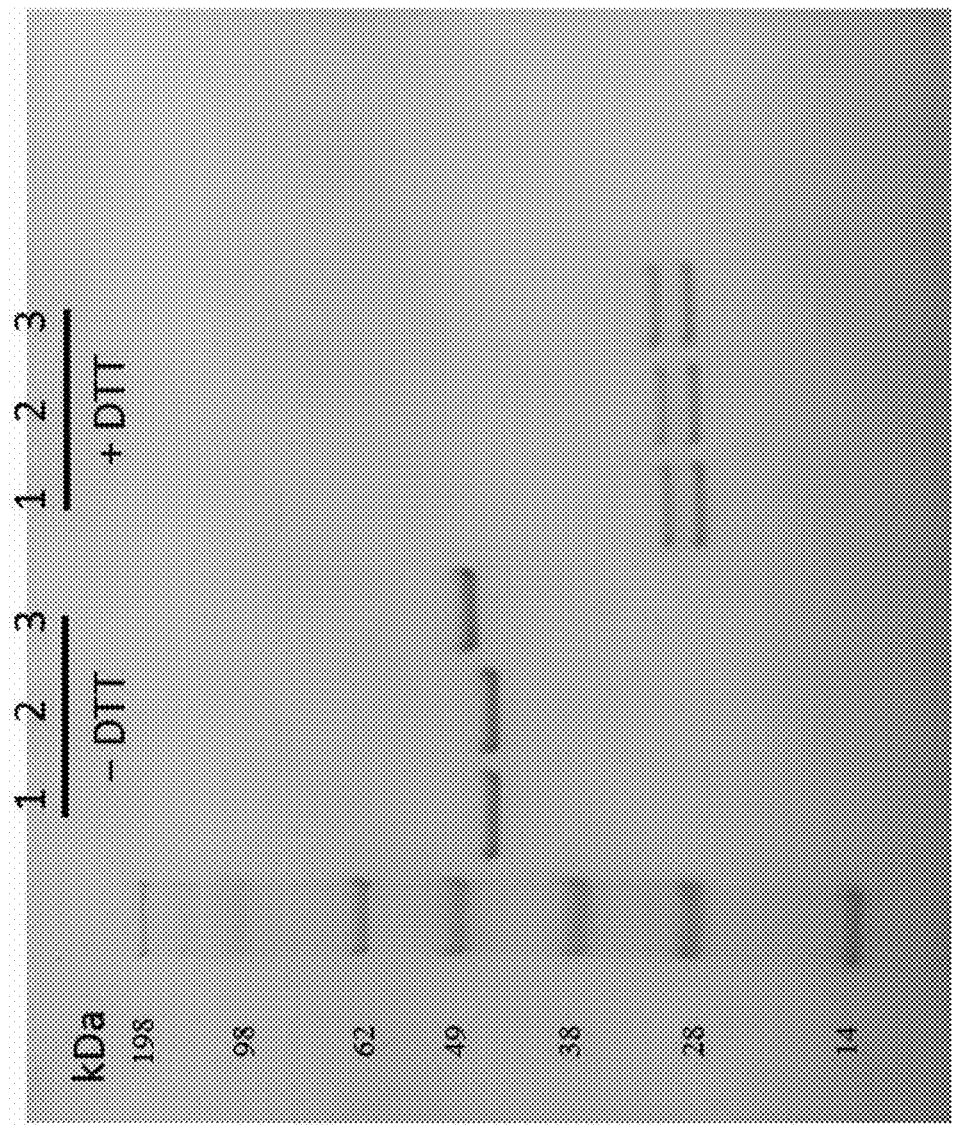
FIG. 8 depicts the results of exemplary experiments demonstrating SDS-PAGE analysis of site-specific αGCN4 Fab conjugates. Lane 1: αGCN4 Fab with double mutations (LC-S155X, HC-K129X; X=pAcF). Lane 2: double-αGCN4 Fab conjugate (LC-S155/HC-K129) with Alexa Fluor 488 dye. Lane 3: double-αGCN4 Fab conjugate (LC-S155/HC-K129) with MMAF toxin.
Figure 13:
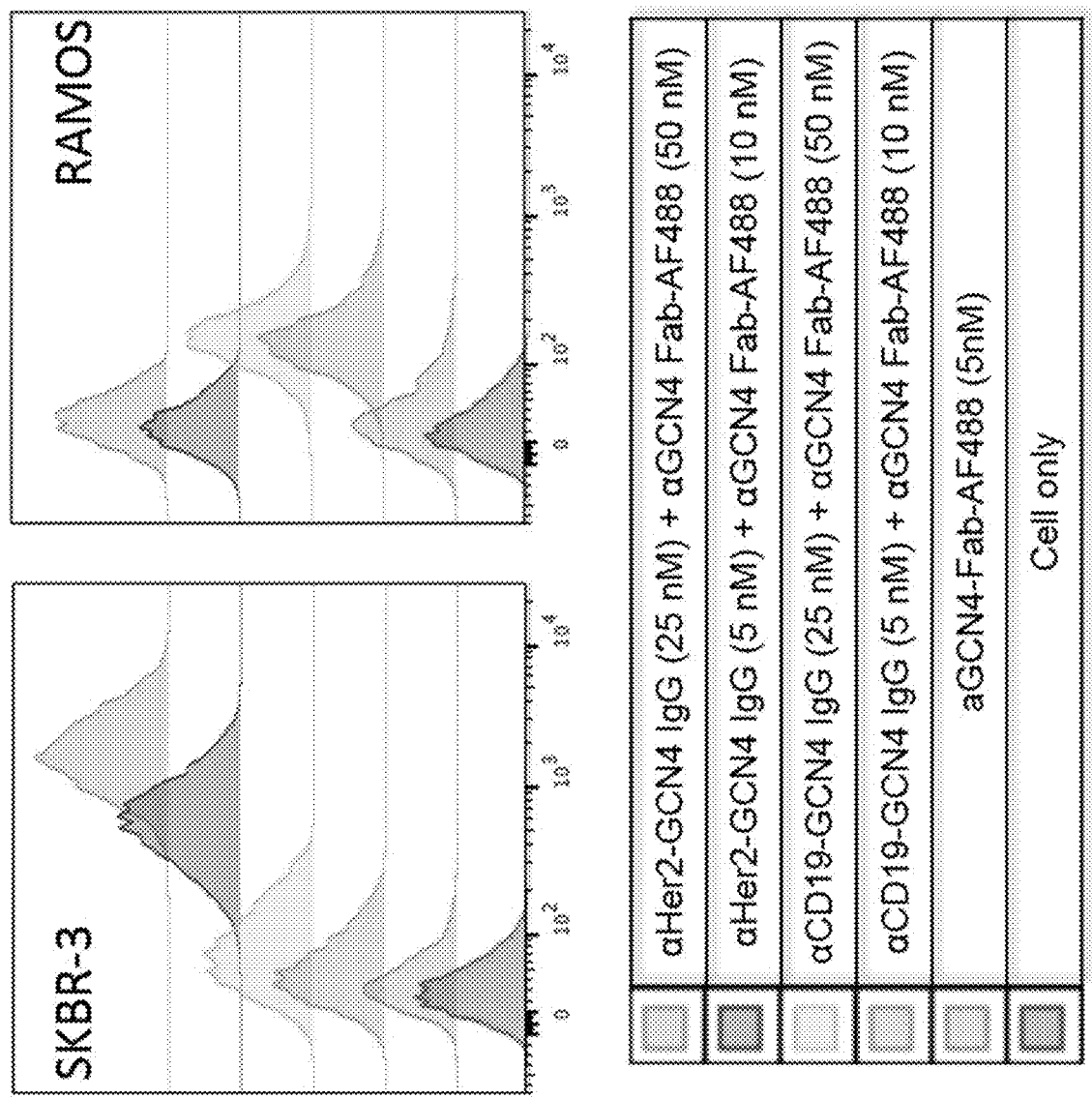
FIG. 13 depicts the results of exemplary experiments demonstrating in vitro detection of cancer cells by flow cytometry using αGCN4-Fab AF488 (LC-S155X, HC-K132X) switched with GCN4-fused αHer2 or αCD19 IgG (CH1 fusion).
Figure 14A:
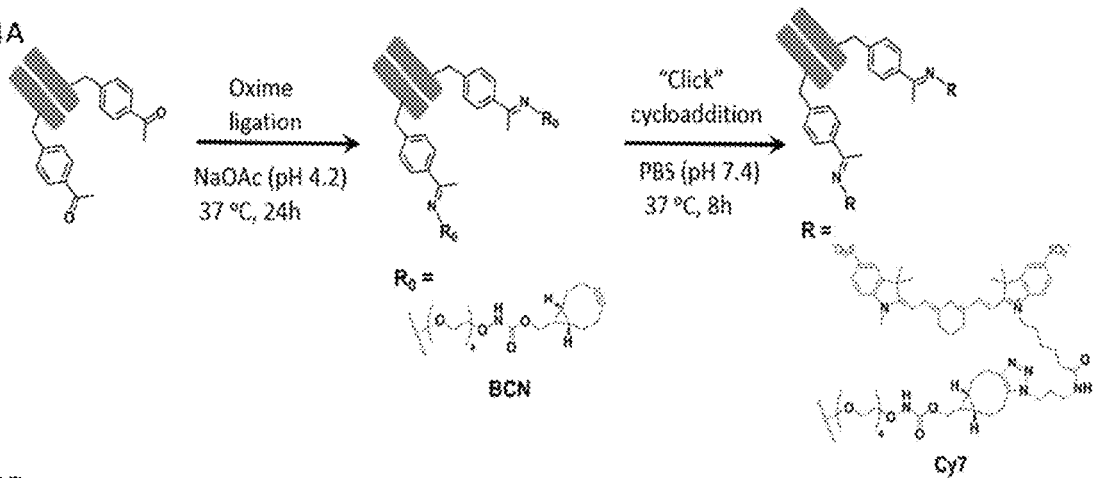
FIG. 14A through FIG. 14D, depicts the results of exemplary experiments demonstrating site-specific conjugation of cyanine 7 (Cy7) dye to αGCN4 Fab (LC-S155X/HC-K129X, X=pAcF).
Figure 14B:
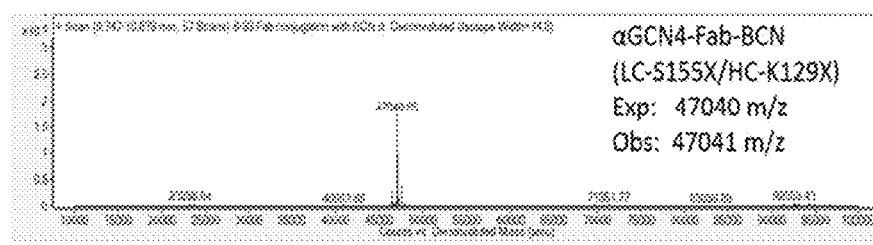
Figure 14C:
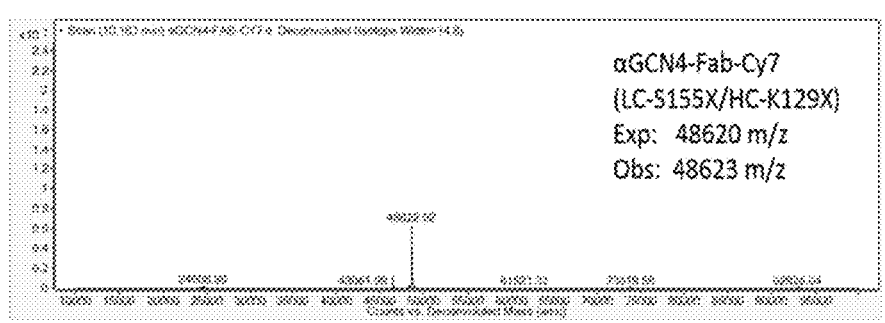
Figure 14D:
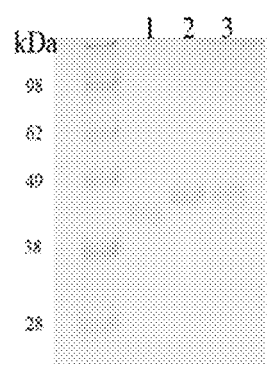

Next, the ability of GCN4 to mediate the detection of different cancer cell lines was tested. Alexa Fluor 488 (AF488) has been commonly used for flow cytometry assays, and was conjugated to αGCN4-Fab (LC-S155X, HC-K129X, X=pAcF) through oxime coupling. The identity and purity of the final αGCN4-Fab-AF488 conjugate was confirmed by ESI-MS (FIG. 12) and SDS/PAGE analysis (FIG. 8). As shown in FIG. 13, the AF488 fluorescence channel can selectively detect SK-BR-3 cells in a dose-responsive manner, when tumor cells were pre-stained by αGCN4-Fab-AF488 and αHer2-HC-GCN4 fusion rather than αGCN4-Fab-AF488 and αCD19-HC-GCN4 fusion. Similarly, Ramos cells can be detected only when they were pre-incubated with αCD19-HC-GCN4 and αGCN4-Fab-AF488. Moreover, the shifts of Ramos cells were weaker than that of SK-BR-3 when both were treated with the same amount of antibody mixtures. This indicates that the CD19 receptor on the Ramos surface may be less intensive than the Her2 receptor on SK-BR-3, which is also consistent with the weaker potencies of antibody conjugates on Ramos cells as revealed by cytotoxicity studies.

Encouraged by these in vitro results, in vivo imaging experiments were performed to further gauge if the GCN4-mediated αGCN4-Fab conjugate can be developed as a switchable imaging agent to efficiently guide cancer therapy. Non-invasive molecular imaging emerges as a powerful tool to accurately and selectively evaluate receptor expression levels, which is crucial for the prediction and timely assessment of the effectiveness of biomarker-targeted cancer therapy (Ehlerding et al., J. Nucl. Med. 2016, 57 (10), 1487-1492). In particular, near-infrared fluorescent (NIRF) imaging allows for deep-penetration and hazard-free imaging of tumor tissues and has been routinely used to delineate tumor margins during surgery (Yi et al., Int. J. Nanomedicine 2014, 9, 1347-1365; Zhang et al., Curr. Protoc. Cytom. 2012, Chapter 12, Unit12 27). Given that the commonly-used NIRF dye Cyanine 7 (Cy7) is stable with azide modifications but not aminooxyl functional groups, a two-step coupling procedure was developed for the synthesis of αGCN4-Fab-Cy7 (FIG. 1, FIG. 14). The first step involved the modification of pAcF on αGCN4-Fab (LC-S155X, HC-K129X, X=pAcF) with an aminooxy-derived BCN linker, followed by desalting chromatography to introduce the azide-reactive BCN moiety at a stoichiometry of two per antibody. The modified αGCN4-Fab (LC-S155X, HC-K129X, X=pAcF-BCN) was then reacted with a 10-fold excess of Cy7-azide (Lumiprobe) at 37° C. for 12 hours. After size-exclusion chromatography purification, the αGCN4-Fab-Cy7 was confirmed by ESI-MS (FIG. 14C) and SDS/PAGE (FIG. 14D) to be >95% pure and has the desired molecular weight with a DAR~2.

Figure 15:
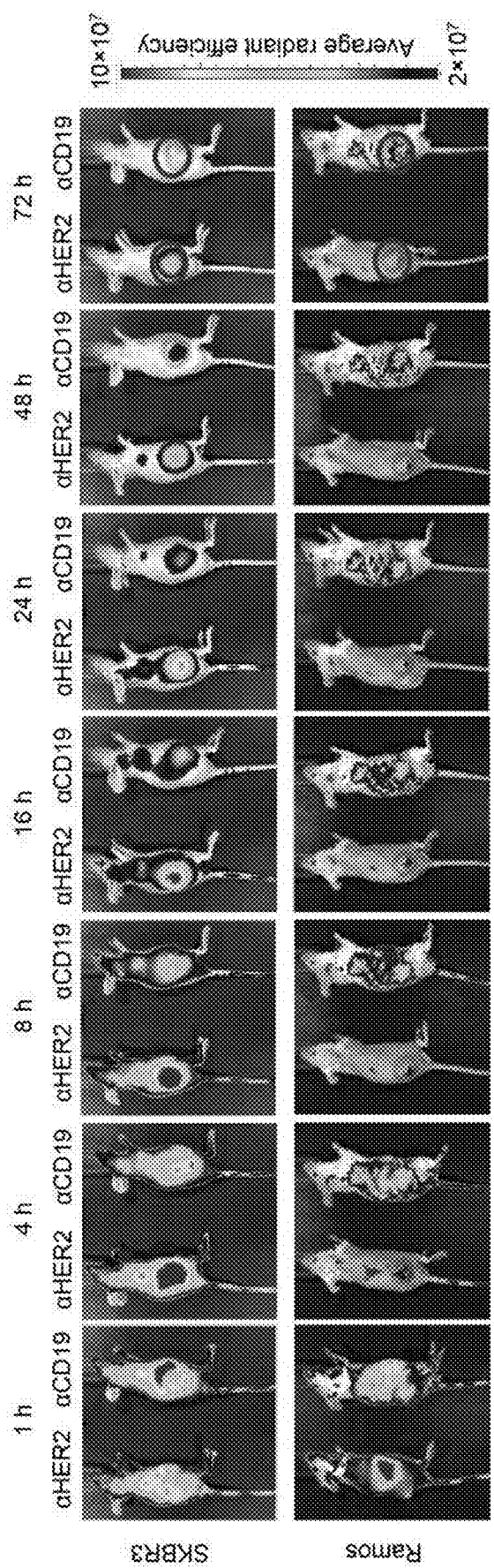
FIG. 15 depicts the results of exemplary experiments demonstrating in vivo near-infrared fluorescence (NIRF) imaging of SKBR3 and Ramos tumor bearing mice after administration of αHER2-HC-GCN4: αGCN4-Cy7(LC-S155X, HC-K132X) or αCD19-HC-GCN4: αGCN4-Cy7 (LC-S155X, HC-K132X).
Figure 16A:
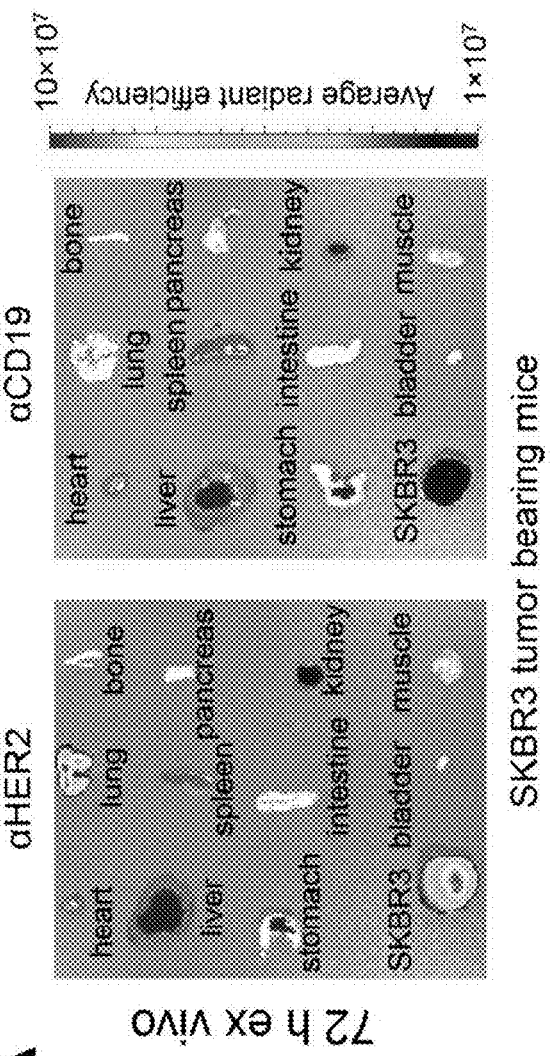
FIG. 16A through FIG. 16B, depicts the results of exemplary experiments demonstrating ex vivo near infrared fluorescence imaging of the organs from tumor xenografts after the administration of either αHer2-GCN4 fusion protein/ αGCN4-Cy7 conjugate or αCD19-GCN4 fusion protein/ αGCN4-Cy7 conjugate.
Figure 16B:
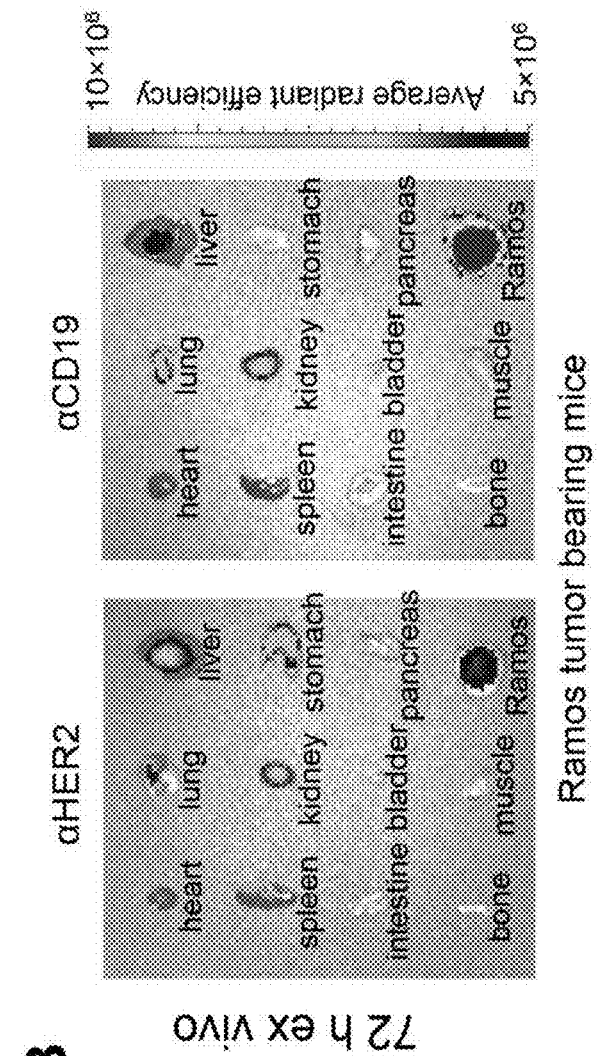

For in vivo NIRF imaging, αGCN4-Fab-Cy7 (1.75 mg/kg) was incubated with either an αHer2-HC-GCN4 fusion or an αCD19-HC-GCN4 fusion (3 mg/kg) at a molar ratio of 2:1, and then injected intravenously into mouse xenografts of SK-BR-3, and Ramos, respectively. The fluorescence signals in tumors increased and became saturated 4 hours post injection (p.i.) (FIG. 15). The whole-body background fluorescence gradually reduced, and became negligible after 24 hours, while the tumor signals remained high till the end of the NIRF scan (72 hours p.i.). As expected, αGCN4-Fab-Cy7 was directed by αHer2-HC-GCN4 to selectively accumulate in the SK-BR-3 tumor instead of Ramos. On the other hand, αCD19-HC-GCN4 effectively directed αGCN4-Fab-Cy7 to the Ramos tumor but not SK-BR-3. Following the last NIRF scan at 72 hours p.i., mice were sacrificed, with tumors and major organs resected for ex vivo NIRF imaging (FIG. 16). The biodistribution data is highly consistent with the in vivo NIRF observation, indicating the antibody probe was selectively enriched in tumors compared to the rest of tissues. Importantly, the stronger fluorescence in breast tumor SK-BR-3 compared to that of Ramos was consistent to the trends observed in the cytotoxicity assay and flow cytometry analysis. Thus, switchable antibody conjugates may ubiquitously probe and distinguish the expression levels of cell-surface biomarkers, thereby serving as a convenient imaging tool.

Figure 17:
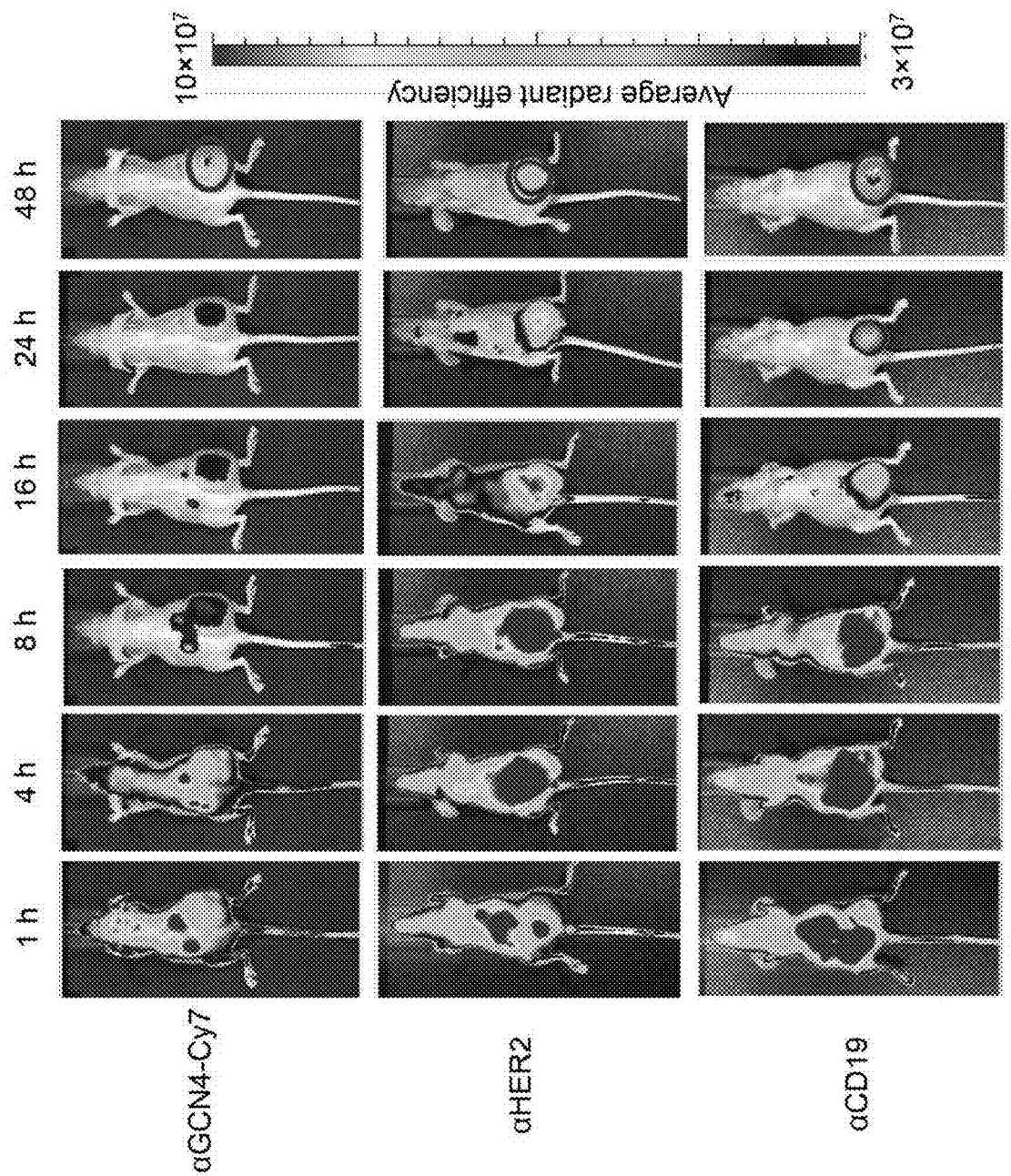
FIG. 17 depicts the results of exemplary experiments demonstrating in vivo pretargeted NIRF imaging of SKBR3 tumor bearing mice after injection with only αGCN4-Cy7 (LC-S155X, HC-K132X), or after pre-injection with αHer2-HC-GCN4 or αCD19-HC-GCN4 followed by (after 4 hours) injection with αGCN4-Cy7(LC-S155X, HC-K132X).

Molecular imaging is also used to directly visualize the targeting process, including bio-distribution and pharmacokinetics (Ehlerding et al., J. Nucl. Med. 2016, 57 (10), 1487-1492; Wang et al., Curr. Mol. Med. 2013, 13 (10), 1523-1537; Guldbrandsen et al., Diagnostics (Basel) 2017, 7 (2), 23). The common approach relies on the direct labeling of immunoconjugates (IgGs) which requires a large dosage to overcome issues of the probe including biostability, photobleaching, and radiodecay (for nuclear imaging) (Yi et al., Int. J. Nanomedicine 2014, 9, 1347-1365; Zhang et al., Curr. Protoc. Cytom. 2012, Chapter 12, Unit12 27; Cook et al., Bioconjug. Chem. 2016, 27 (8), 1789-1795). Pre-targeted imaging was recently proposed to improve tumor signal-to-background ratio and to reduce the dosage requirement, so that there will be limited systemic exposure to harmful effects of the agent. Without being bound by theory, it was reasoned that the Fab-based αGCN4 conjugates could serve as a secondary diagnostic agent while the GCN4-tagged primary IgG could be a pre-targeting agent. In a pilot experiment with NIRF imaging, 3 mg (18 nmol)/kg αHer2-HC-GCN4 or αCD19-HC-GCN4 was injected as a pre-targeting agent to SK-BR-3 breast cancer bearing mouse xenografts which showed better imaging signals than Ramos mouse xenografts. After ~4 hours, during which the tumor could be maximally bound by the primary IgG, the injection of αGCN4-Fab-Cy7 at 1.75 mg (36 nmol)/kg was begun and monitored the NIRF thereafter. For the control group that was injected with only αGCN4-Fab-Cy7, the background fluorescence quickly cleared out and became negligible at the end of 48 hours (FIG. 17), which could be due to the short half-life of Fab fragments. With the pre-targeting of αCD19-HC-GCN4, the fluorescence signal was initially strong (1 hour-8 hour post injection of Fab), thereby reflecting the GCN4-mediated recognition of αCD19 IgG by αGCN4-Fab-Cy7 in the circulating blood. However, the signal eventually decreased to a negligible level at 48 hours p.i., presumably because the αCD19 IgG failed to specifically recognize the breast cancer tumor. Only with pre-targeted recognition of the Her2-positive SK-BR-3 by αHer2-HC-GCN4, αGCN4-Fab-Cy7 can be enriched in the tumor region, which displayed strong fluorescence signal from 16 hours to 48 hours p.i (FIG. 17). These results showed that the GCN4-mediated site-specific antibody conjugates can also be used for pre-targeted tumor imaging.

In conclusion, these experiments have demonstrated the development of a switchable site-specific antibody conjugate based on the genetically encoded unnatural amino acid p-acetylphenylalanine (pAcF). This antibody conjugate was optimized with a fixed site and stoichiometry, and specifically recognizes a GCN4 peptide tag that is orthogonal to human proteins. Using GCN4 as a switch, the antibody conjugate can be directed by different primary IgGs to target the cognate biomarkers unique to different tumors. With various payloads such as a toxin drug or imaging probes, this switchable approach demonstrated promising effects and flexibility in therapeutic treatment and imaging-guided diagnosis of breast cancer and B-cell lymphoma. Further evaluation of the conjugate's in vivo efficacy on tumor growth inhibition is currently ongoing to determine its therapeutic potential. In addition, a radiolabeled αGCN4 Fab-NOTA conjugate can be used for pretargeted positron emission tomography (PET) imaging (Cook et al., Bioconjug. Chem. 2016, 27 (8), 1789-1795). Finally, this work suggests that with an orthogonal switch, a fixed antibody conjugate can be used to rapidly deliver small molecule drugs, oligonucleotides, peptides or proteins in the future to a diverse set of tumors, thereby facilitating diagnosis and/or therapeutic treatment.

Example 2: Antibody Sequences

```
SEQ ID NO: 3 Anti-Her2 trastuzumab light chain:
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

SEQ ID NO: 4 Anti-Her2 trastuzumab light chain GCN4 (graft and linker underlined):
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKLEIKRTVAAPSVFIFPPSDEQLKSGTASVVCLLNNFYPREAKVQWKV

DNALQSGNSQESVTEQDSGGGGSNYHLENEVARLKKLGGGGSDSTYSLSS

TLTLSKADYEKHKVYACEVTHQGLSSPVTKSFNRGEC

SEQ ID NO: 5 Anti-Her2 trastuzumab heavy chain (up to CH1):
EVQLVESGGGLVQPGGSLRLSCAASGFNIKDTYIHWVRQAPGKGLEWVAR

TYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSC

SEQ ID NO: 6 Anti-Her2 trastuzumab heavy chain GCN4 (up to CH1, graft and linker underlined):
EVQLVESGGGLVQPGGSLRLSCAASGFNIKDTYIHWVRQAPGKGLEWVAR

TYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSGGGGSNYHLENEVARLKKLGG

GGSLYSLSSVVTVPSSSLGTQTYICNVNHKPSNTKVDKKVEPKSC

SEQ ID NO: 7 Anti-CD19 FMC63 light chain:
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 8 Anti-CD19 FMC63 light chain GCN4 (graft and linker underlined):
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIKRTVAAPSVFIFPPSDEQLKSGTASVVCLLNNFYPREAKVQWKV

DNALQSGNSQESVTEQDSGGGGSNYHLENEVARLKKLGGGGSDSTYSLSS

TLTLSKADYEKHKVYACEVTHQGLSSPVTKSFNRGEC

SEQ ID NO: 9 Anti-CD19 FMC63 heavy chain (up to CH1):
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSC

SEQ ID NO: 10 Anti-CD19 FMC63 heavy chain GCN4 (up to CH1, graft and linker underlined):
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSASTKGPSVFPLAPSSKSTSGGTAALGCLVK

DYFPEPVTVSWNSGALTSGVHTFPAVLQSGGGGSNYHLENEVARLKKLGG

GGSLYSLSSVVTVPSSSLGTQTYICNVNHKPSNTKVDKKVEPKSC

SEQ ID NO: 11 Anti-GCN4 Fab light chain
DAVVTQESALTSSPGETVTLTCRSSTGAVTTSNYASWVQEKPDHLFTGLI

GGTNNRAPGVPARFSGSLIGDKAALTITGAQTEDEAIYFCVLWYSDHWVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

SEQ ID NO: 12 Anti-GCN4 Fab heavy chain
DVQLQESGPGLVAPSQSLSITCTVSGFLLTDYGVNWVRQSPGKGLEWLGV

IWGDGITDYNSALKSRLSVTKDNSKSQVFLKMNSLQSGDSARYYCVTGLF

DYWGQGTTLTVSSASTKGPSVFPLAPSSKSTSGGTAALGCLVKDYFPEPV

TVSWNSGALTSGVHTFPAVLQSSGLYSLSSVVTVPSSSLGTQTYICNVNH

KPSNTKVDKKVEPKSCDKTHT

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a site-specific conjugate molecule, wherein the site-specific conjugate molecule comprises an immunoconjugate molecule comprising a polypeptide component and at least one conjugated molecule, wherein the polypeptide component comprises an antigen binding domain comprising an anti-GCN4 Fab fragment comprising the light chain amino acid sequence of SEQ ID NO:11 and heavy chain amino acid sequence of SEQ ID NO:12, bound to a targeting molecule, wherein the targeting molecule comprises targeting domain for binding to a target of interest and a immunoconjugate-antigen domain for recognition by the antigen binding domain of the immunoconjugate molecule, wherein the immunoconjugate molecule is bound to the targeting molecule through the interaction of the antigen binding domain of the polypeptide component of the immunoconjugate molecule with the immunoconjugate-antigen domain of the targeting molecule.

2. The composition of claim 1, wherein the immunoconjugate-antigen domain is a GCN4 peptide.

3. A method of detecting a target molecule in a sample from a subject comprising the steps of:
   a) contacting the sample with at least one composition comprising a targeting molecule, wherein the targeting molecule comprises a targeting domain for binding to a target of interest and an immunoconjugate-antigen domain for recognition by an antigen binding domain of an immunoconjugate molecule,
   b) contacting the sample with at least one composition comprising a site-specific conjugate molecule of claim 1, and
   c) analyzing the sample.

4. The method of claim 3, wherein at least one conjugated molecule is a detectable molecule.

5. A method of treating a HER2 positive breast cancer in a subject in need thereof, the method comprising the steps of:
   a) administering to the subject at least one composition comprising a targeting molecule, wherein the targeting molecule comprises a targeting domain for binding to a target of interest and an immunoconjugate-antigen domain for recognition by an antigen binding domain of an immunoconjugate molecule, wherein the targeting molecule specifically binds to an antigen associated with the disease or disorder; and
   b) administering to the subject at least one composition comprising a site-specific conjugate molecule of claim 1, wherein at least one conjugated molecule is a therapeutic agent for the treatment of HER2 positive breast cancer.

6. The method of claim 5, wherein the targeting molecule is fused to the immunoconjugate molecule prior to administration.

* * * * *